United States Patent
Sato et al.

(10) Patent No.: US 7,405,271 B2
(45) Date of Patent: Jul. 29, 2008

(54) ALKALINE PROTEASE

(75) Inventors: Tsuyoshi Sato, Tochigi (JP); Mitsuyoshi Okuda, Tochigi (JP); Shingo Koyama, Kamisu-machi (JP); Yoshifumi Izawa, Tochigi (JP); Tohru Kobayashi, Tochigi (JP)

(73) Assignee: Kao Corporation, Tokyo (JP)

( * ) Notice: Subject to any disclaimer, the term of this patent is extended or adjusted under 35 U.S.C. 154(b) by 223 days.

(21) Appl. No.: 10/820,712

(22) Filed: Apr. 9, 2004

(65) Prior Publication Data

US 2005/0026804 A1 Feb. 3, 2005

(30) Foreign Application Priority Data

Apr. 10, 2003 (JP) ............................. 2003-106708

(51) Int. Cl.
*C07K 1/00* (2006.01)
(52) U.S. Cl. .................. 530/350; 530/300; 435/221; 435/7.1
(58) Field of Classification Search ........................ None
See application file for complete search history.

(56) References Cited

U.S. PATENT DOCUMENTS 6,803,222 B2 * 10/2004 Hatada et al. ................ 435/212
7,101,698 B2 * 9/2006 Sato et al. .................... 435/221

FOREIGN PATENT DOCUMENTS

| EP | 1 209 233 | 5/2002 |
|---|---|---|
| WO | WO 87/05050 | 8/1987 |
| WO | WO 98/56927 | 12/1998 |
| WO | WO 99/11768 | 3/1999 |
| WO | WO 99/18218 | 4/1999 |

OTHER PUBLICATIONS

Wells, Biochemistry, vol. 29, pp. 8509-8517, 1990.*
Seffernick et al. (J. Bacteriology, vol. 183, pp. 2405-2410, 2001).*
C. Schmidt-Danner, et al., Trends in Biotechnology, vol. 17, No. 4, XP 004162829, pp. 135-136, "Directed Evolution of Industrial Enzymes", Apr. 1999.
K. Saeki, et al., Biochemical and Biophysical Research Communications, vol. 279, No. 2, pp. 313-319, "Novel Oxidatively Stable Subtilisin-Like Serine Proteases From Alkaliphilic *Bacillus* spp.: Enzymatic Properties, Sequences, and Evolutionary Relationships", 2000.

* cited by examiner

*Primary Examiner*—Hope A Robinson
(74) *Attorney, Agent, or Firm*—Oblon, Spivak, McClelland, Maier & Neustadt, P.C.

(57) ABSTRACT

An alkaline protease having an amino acid with one or more amino acid residues selected from among those located at (a) position 63, (b) position 89, (c) position 120, (d) positions 63 and 187, (e) position 226, (f) position 296, (g) position 304 of the amino acid sequence of SEQ ID NO: 1, or at positions corresponding to these positions, are the following amino acid residues, respectively: (a): serine, (b): histidine, (c): arginine, (d): serine,(e): tyrosine, (f): valine, and (g): serine; and a gene encoding the alkaline protease.

2 Claims, 7 Drawing Sheets

```
KP43     1:NDVARGIVKADVAQSSYGLYGQGQIVAVADTGLDTGRNDSSMHEA  45
KP9860   1:NDVARGIVKADVAQSSYGLYGQGQIVAVADTGLDTGRNDSSMHEA  45
KP9865   1:NDVARGIVKADVAQSSYGLYGQGQIVAVADTGLDTGRNDSSMHEA  45
E-1      1:NDVARGIVKADVAQNNYGLYGQGQIVAVADTGLDTGRNDSSMHEA  45
Ya       1:NDVARGIVKADVAQNNYGLYGQGQIVAVADTGLDTGRNDSSMHEA  45
SD-521   1:NDVARGIVKADVAQNNYGLYGQGQVVAVADTGLDTGRNDSSMHEA  45
A-1      1:NDVARGIVKADVAQSSYGLYGQGQVVAVADTGLDTGRNDSSMHEA  45
A-2      1:NDVARGIVKADVAQNNFGLYGQGQIVAVADTGLDTGRNDSSMHEA  45
           ************** .**** ********************

KP43    46:FRGKITALYALGRTNNANDTNGHGTHVAGSVLGNGSTNKGMAPQA  90
KP9860  46:FRGKITALYALGRTNNANDTNGHGTHVAGSVLGNGATNKGMAPQA  90
KP9865  46:FRGKITALYALGRTNNANDTNGHGTHVAGSVLGNGSTNKGMAPQA  90
E-1     46:FRGKITALYALGRTNNANDPNGHGTHVAGSVLGNALNKG-MAPQA  89
Ya      46:FRGKITALYALGRTNNANDPNGHGTHVAGSVLGNALNKG-MAPQA  89
SD-521  46:FRGKITALYALGRTNNASDPNGHGTHVAGSVLGNALNKG-MAPQA  89
A-1     46:FRGKITAIYALGRTNNANDPNGHGTHVAGSVLGNGTSNKGMAPQA  90
A-2     46:FRGKITALYALGRTNNANDPNGHGTHVAGSVLGNATNK-GMAPQA  89
           *******:********:.*.********** .     ******
```

FIG1-1

```
KP43    91:NLVFQSIMDSGGGLGGLPSNLQTLFSQAYSAGARIHTNSWGAAVN 135
KP9860  91:NLVFQSIMDSSGGLGGLPSNLQTLFSQAYSAGARIHTNSWGAAVN 135
KP9865  91:NLVFQSIMDSGGGLGGLPSNLQTLFSQAFSAGARIHTNSWGAAVN 135
E-1     90:NLVFQSIMDSSGGLGGLPSNLNTLFSQAYSAGARIHTNSWGAAVN 134
Ya      90:NLVFQSIMDSSGGLGGLPSNLNTLFSQAWNAGARIHTNSWGAPVN 134
SD-521  90:NLVFQSIMDSSGGLGGLPSNLNTLFSQAWNAGARIHTNSWGAPVN 134
A-1     91:NLVFQSVMDSNGGLGGLPSNVSTLFSQAYSAGARIHTNSWGAPVN 135
A-2     90:NLVFQSIMDSGGGLGGLPANLQTLFSQAYSAGARIHTNSWGAPVN 134
           *****.***.********.*.*******.**********.**

KP43    136:GAYTTDSRNVDDYVRKNDMTILFAAGNEGPNGGTISAPGTAKNAI 180
KP9860  136:GAYTTDSRNVDDYVRKNDMTILFAAGNEGPNGGTISAPGTAKNAI 180
KP9865  136:GAYTTDSRNVDDYVRKNDMTILFAAGNEGPNGGTISAPGTAKNAI 180
E-1     135:GAYTANSRQVDEYVRNNDMTVLFAAGNEGPNSGTISAPGTAKNAI 179
Ya      135:GAYTANSRQVDEYVRNNDMTVLFAAGNEGPNSGTISAPGTAKNAI 179
SD-521  135:GAYTANSRQVDEYVRNNDMTVLFAAGNEGPNSGTISAPGTAKNAI 179
A-1     136:GAYTTDSRNVDDYVRKNDMAVLFAAGNEGPNGGTISAPGTAKNAI 180
A-2     135:GAYTTDSRNVDDYVRKNDMTILFAAGNEGPGSGTISAPGTAKNAI 179
           ****..**.***.***.***.********..*************

FIG1-2
```

```
KP43    181:TVGATENLRPSFGSYADNINHVAQFSSRGPTKDGRIKPDVMAPGT 225
KP9860  181:TVGATENLRPSFGSYADNINHVAQFSSRGPTKDGRIKPDVMAPGT 225
KP9865  181:TVGATENLRPSFGSYADNINHVAQFSSRGPTKDGRIKPDVMAPGT 225
E-1     180:TVGATENYRPSFGSIADNPNHIAQFSSRGATRDGRIKPDVTAPGT 224
Ya      180:TVGATENYRPSFGSIADNPNHIAQFSSRGATRDGRIKPDVTAPGT 224
SD-521  180:TVGATENYRPSFGSLADNPNHIAQFSSRGPTKDGRIKPDVTAPGT 224
A-1     181:TVGATENLRPSFGSYADNINHVAQFSSRGPTKDGRIKPDVMAPGT 225
A-2     180:TVGATENLRPSFGSYADNINHVAQFSSRGPTRDGRIKPDVMAPGT 224
            ********.***** ***.**.*********. ********.****

KP43    226:FILSARSSLAPDSSFWANHDSKYAYMGGTSMATPIVAGNVAQLRE 270
KP9860  226:YILSARSSLAPDSSFWANHDSKYAYMGGTSMATPIVAGNVAQLRE 270
KP9865  226:FILSARSSLAPDSSFWANHDSKYAYMGGTSMATPIVAGNVAQLRE 270
E-1     225:FILSARSSLAPDSSFWANYNSKYAYMGGTSMATPIVAGNVAQLRE 269
Ya      225:FILSARSSLAPDSSFWANYNSKYAYMGGTSMATPIVAGNVAQLRE 269
SD-521  225:FILSARSSLAPDSSFWANHDSKYAYMGGTSMATPIVAGNVAQLRE 269
A-1     226:FILSARSSLAPDSSFWANHDSKYAYMGGTSMATPIVAGNVAQLRE 270
A-2     225:YILSARSSLAPDSSFWANHDSKYAYMGGTSMATPIVAGNVAQLRE 269
            .*****************..********************
```

FIG1-3

```
KP43     271: HFVKNRGITPKPSLLKAALIAGAADIGLGYPNGNQGWGRVTLDKS  315
KP9860   271: HFVKNRGITPKPSLLKAALIAGAADVGLGYPNGNQGWGRVTLDKS  315
KP9865   271: HFVKNRGITPKPSLLKAALIAGAADIGLGYPNGNQGWGRVTLDKS  315
E-1      270: HFIKNRGITPKPSLIKAALIAGATDVGLGYPSGDQGWGRVTLDKS  314
Ya       270: HFIKNRGITPKPSLLKAALIAGATDVGLGYPNGDQGWGRVTLNKS  314
SD-521   270: HFIKNRGITPKPSLLKAALIAGATDVGLGYPSGDQGWGRVTLDKS  314
A-1      271: HFIKNRGITPKPSLLKAALIAGATDIGLGYPSGNQGWGRVTLDKS  315
A-2      270: HFVKNRGVTPKPSLLKAALIAGAADVGLGFPNGNQGWGRVTLDKS  314
              **  ****.*******.********.*.*.****...********

KP43     316: LNVAYVNESSSLSTSQKATYSFTATAGKPLKISLVWSDAPASTTA  360
KP9860   316: LNVAYVNESSALSTSQKATYFFTATAGKPLKISLVWSDAPASTTA  360
KP9865   316: LNVAYVNESSSLSTSQKATYSFTATAGKPLKISLVWSDAPASTTA  360
E-1      315: LNVAYVNEATALTTGQKATYSFQTQAGKPLKISLVWTDAPGSTTA  359
Ya       315: LNVAYVNEATALATGQKATYSFQAQAGKPLKISLVWTDAPGSTTA  359
SD-521   315: LNVAYVNEATALATGQKATYSFQAQAGKPLKISLVWSDAPASTTA  359
A-1      316: LNVAFVNETSSLSTNQKATYSFTAQSGKPLKISLVWSDAPASTSA  360
A-2      315: LNVAFVNETSPLSTSQKATYSFTAQAGKPLKISLVWSDAPGSTTA  359
              ****.***  *.** ..***** .*.. ********.***.**.*
```

FIG1-4

```
KP43    361:SVTLVNDLDLVITAPNGTQYVGNDFTSPYNDNWDGRNNVENVFIN 405
KP9860  361:SVTLVNDLDLVITAPNGTRYVGNDFSAPFDNNWDGRNNVENVFIN 405
KP9865  361:SVTLVNDLDLVITAPNGTQYVGNDFTSPYNNNWDGRNNVENVFIN 405
E-1     360:SYTLVNDLDLVITAPNGQKYVGNDFSYPYDNNWDGRNNVENVFIN 404
Ya      360:SYTLVNDLDLVITAPNGQKYVGNDFSYPYDNNWDGRNNVENVFIN 404
SD-521  360:SYTLVNDLDLVITAPNGTKYVGNDFSYPYDNNWDGRNNVENVFIN 404
A-1     361:SVTLVNDLDLVITAPNGTKYVGNDFTAPYDNNWDGRNNVENVFIN 405
A-2     360:SLTLVNDLDLVITAPNGTKYVGNDFTAPYDNNWDGRNNVENVFIN 404
           * ***********..****** *...***************

KP43    406:APQSGTYTIEVQAYNVPVGPQTFSLAIVN 434
KP9860  406:SPQSGTYTIEVQAYNVPVGPQNFSLAIVN 434
KP9865  406:APQSGTYTIEVQAYNVPVGPQTFSLAIVN 434
E-1     405:APQSGTYTIEVQAYNVPSGPQRFSLAIVH 433
Ya      405:APQSGTYIIEVQAYNVPSGPQRFSLAIVH 433
SD-521  405:APQSGTYTVEVQAYNVPSGPQRFSLAIVH 433
A-1     406:APQSGTYTVEVQAYNVPQGPQAFSLAIVN 434
A-2     405:APQSGTYTVEVQAYNVPVSPQTFSLAIVH 433
           ******..*.*******. ** ******
```

FIG1-5

ALKALINE PROTEASE

CROSS-REFERENCE TO RELATED APPLICATION

This application claims the benefit to priority under 35 U.S.C. §119(a)-(d) to JP 2003-106708, filed Apr. 10, 2003.

FIELD OF THE INVENTION

The present invention relates to an alkaline protease and to a gene encoding the same.

BACKGROUND OF THE INVENTION

Protease has long been used in industry, and has found utility in a diversity of fields, including detergents such as laundry detergents, fiber modifying agents, leather processing agents, cosmetic compositions, bath additives, food-modifying agents, and pharmaceuticals. Of these, proteases for detergent use are produced in the largest amounts on an industrial scale. Examples of such known proteases that are derived from *bacillus* include ALCALASE, SAVINASE (registered trademarks; Novozymes), MAXACAL (registered trademark; Genencor), BLAP (registered trademark; Henkel), and KAP (Kao Corporation).

The purpose of incorporating protease into a detergent is to degrade protein soil adhering to clothes. Such soil actually is a "complex" soil formed of a plurality of organic and inorganic components, including not only proteins but also lipids originating from sebum, solid particles, and other substances. Therefore, demand has arisen for a detergent having excellent detergency against such complex soil.

Under the above situation, some of the present inventors have previously discovered several species of alkaline protease which have a molecular weight of about 43,000, exhibit a sufficient casein-degrading activity even in the presence of a fatty acid at a high concentration, and also exhibit excellent detergency not only to proteins but also to complex soils which include sebum and other substances, and filed a patent application therefor (see Patent Publication WO99/18218). Since the discovered alkaline proteases differ from subtilisin (which is a conventionally known serine protease derived from a microorganism belonging to the genus *Bacillus*) in terms of molecular weight, primary structure, enzymological characteristics and resistance to oxidants (the alkaline proteases are strongly resistant to oxidants) their classification into a new subtilisin subfamily has been proposed (Saeki et al., Biochem. Biophys. Res. Commun., 279, 313-319, 2000).

Incorporating such proteases into a detergent requires several steps, including concentration of a culture, drying, and granulation. Also, deactivation of proteases, which may otherwise occur during storage of the detergent, must be prevented.

In addition, researchers have recognized the problem that when a gene coding for such a protease is modified to give mutants having an enhanced specific activity and high production, some of such mutants show thermal stability lower than that of a protease before undergoing mutation. Thus, there has arisen a demand to improve thermal stability of the enzymes to solve the mentioned problems.

Accordingly, the present invention provides an alkaline protease which has excellent detergency against complex soil as well as enhanced thermal stability.

SUMMARY OF THE INVENTION

The present invention provides an alkaline protease having an amino acid sequence wherein one or more amino acid residues selected from those located at (a) position 63, (b) position 89, (c) position 120, (d) positions 63 and 187, (e) position 226, (f) position 296, (g) position 304 of the amino acid sequence of SEQ ID NO: 1, or at positions corresponding to these positions are the following amino acid residues, respectively:
Position (a): serine,
Position (b): histidine,
Position (c): arginine
Position (d): serine,
Position (e): tyrosine,
Position (f): valine, and
Position (g): serine.

The present invention also provides a gene encoding the alkaline protease.

The present invention also provides a vector comprising the gene, and a transformant containing the vector.

The present invention also provides a detergent composition containing the above-described alkaline protease.

BRIEF DESCRIPTION OF THE DRAWINGS

FIG. 1-1 to FIG. 1-5 shows amino acid sequence alignment of protease having 80% or higher homology with the amino acid sequence of SEQ ID NO: 1.

FIG. 2 shows improvement in thermal stability of the alkaline protease of an embodiment of the present invention after treatment at 70° C. for 10 minutes in a borate buffer (pH 10, 50 mM).

FIG. 3 shows improvement in thermal stability of the alkaline protease of an embodiment of the present invention after treatment at 80° C. for 10 minutes in 2 mM calcium chloride.

DETAILED DESCRIPTION OF THE INVENTION

Figure 2:
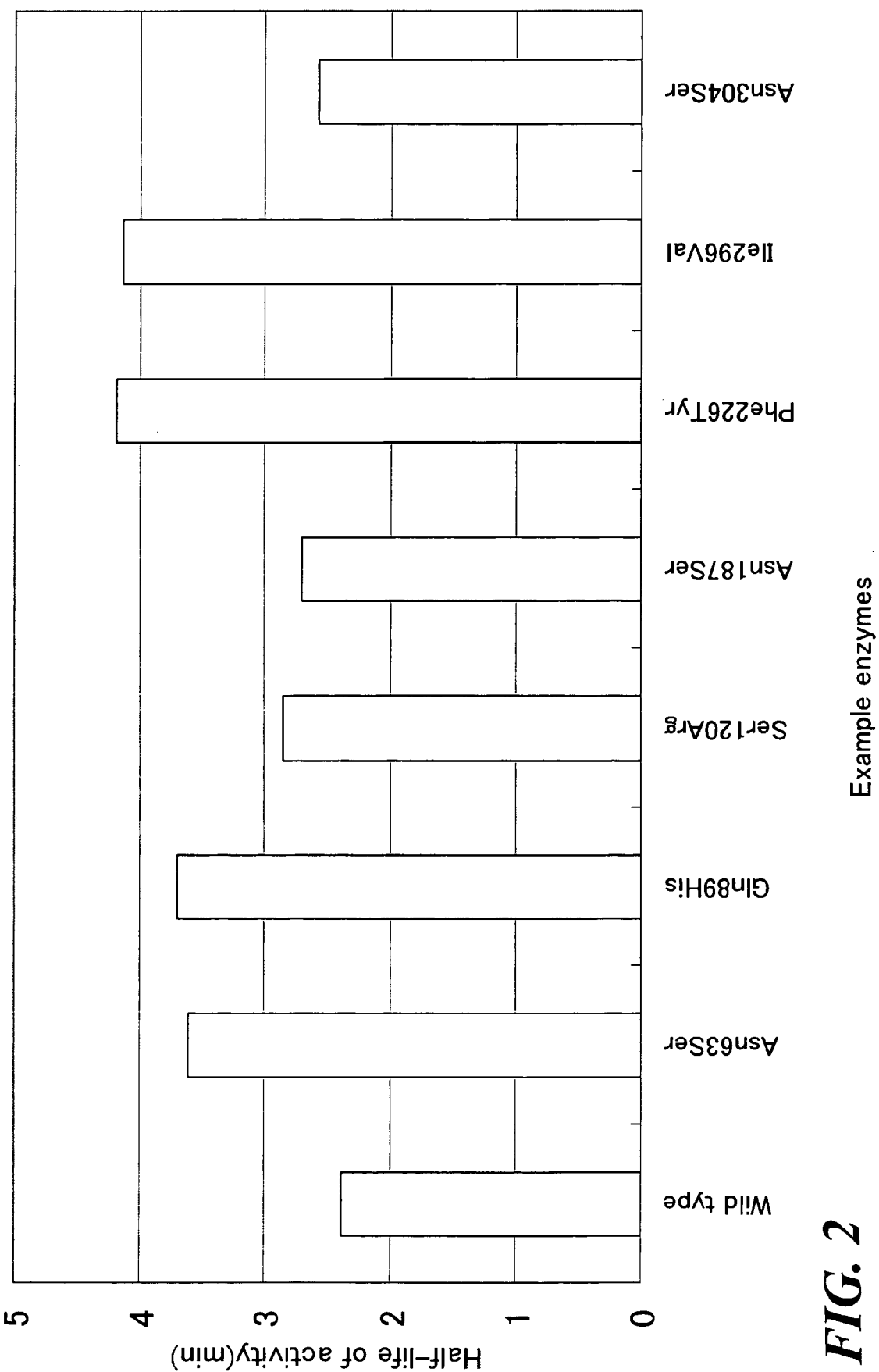

The present inventors have searched for a new enzyme which is endowed with the characteristics of the aforementioned alkaline protease and also with for example, improved thermal stability, and have found that such an enzyme, which is a certain alkaline protease, requires the presence of specified amino acid residue(s) at specified position(s) of the amino acid sequence of the alkaline protease.

The alkaline protease of the present invention has an amino acid sequence wherein one or more amino acid residues selected from those located at (a) position 63, (b) position 89, (c) position 120, (d) positions 63 and 187, (e) position 226, (f) position 296, (g) position 304 of the amino acid sequence of SEQ ID NO: 1, or at positions corresponding to these positions are the following amino acid residues, respectively:
position (a): serine, position (b): histidine, position (c): arginine, position (d): serine, position (e): tyrosine, position (f): valine, and position(g): serine.

Namely, the alkaline protease of the present invention is a protease that has been engineered such that one or more amino acid residues selected from the above-mentioned positions (a) to (g) of an alkaline protease having an amino acid sequence of SEQ ID NO: 1, or amino acid residue(s) of another alkaline protease at position(s) corresponding to the above-mentioned positions (a) to (g), are specified amino acid residue(s), and may be of a wild type, mutant(s) of the wild type, or mutant(s) created by artificial mutagenesis.

As used herein, "another alkaline protease" may be either a wild type enzyme or a mutant of the wild type enzyme.

Preferably, "another alkaline protease" exhibits resistance to oxidants and has a molecular weight of 43,000±2,000 as determined by SDS-PAGE (sodium dodecylsulfate polyacrylamide gel electrophoresis), and as an example thereof, mention may be given of an alkaline protease having such an amino acid sequence that exhibits 80% or higher homology with the amino acid sequence of SEQ ID NO: 1. More preferably, "another alkaline protease" is an enzyme which has an amino acid sequence that exhibits 80% or higher homology with the amino acid sequence of SEQ ID NO: 1; acts in an alkaline region of pH 8 or higher; exhibits resistance to oxidants; shows 80% or higher residual activity after treatment at 50° C. for 10 minutes at pH 10; is inhibited by diisopropylfluorophosphate (DFP) and phenylmethanesulfonyl fluoride (PMSF); and has a molecular weight of 43,000±2,000 as determined by SDS-PAGE. As used herein, the expression "exhibit resistance to oxidants" means that after an alkaline protease is left to stand at 30° C. for 20 minutes in 20 mM Britton-Robinson buffer (pH 10) containing 50 mM hydrogen peroxide and 5 mM calcium chloride, the alkaline protease maintains a residual activity of at least 50%.

Examples of the "alkaline protease having an amino acid sequence of SEQ ID NO: 1" include KP43 (derived from *Bacillus* sp. KSM-KP43 (FERM BP-6532), Patent Publication WO99/18218). Examples of the "alkaline protease having an amino acid sequence that exhibits 80% or higher homology with the amino acid sequence of SEQ ID NO: 1" include protease KP9860 (GenBank Accession No. AB046403) (derived from *Bacillus* sp. KSM-KP9860 (FERM BP-6534), International Patent Publication WO99/18218) (SEQ ID NO: 11 and 12); protease 9865 (GenBank Accession No. AB084155) (derived from *Bacillus* sp. KSM-9865 (FERM P-1592), Japanese Patent Application Laid-Open (kokai) No. 2003-199559) (SEQ ID NO: 13 and 14); protease E-1 (GenBank Accession No. AB046402) (derived from *Bacillus* No. D-6 (FERM P-1592), Japanese Patent Application Laid-Open (kokai) No. 49-71191) (SEQ ID NO: 15 and 16); protease Ya (GenBank Accession No. AB046404) (derived from *Bacillus* sp. Y (FERM BP-1029), Japanese Patent Application Laid-Open (kokai) No. 61-280268) (SEQ ID NO: 17 and 18); protease SD521 (GenBank Accession No. AB046405) (derived from *Bacillus* SD521 (FERM P-11162), Japanese Patent Application Laid-Open (kokai) No. 3-191781) (SEQ ID NO: 19 and 20); protease A-1 (GenBank Accession No. AB046406) (derived from NCIB12289, Patent Publication WO88/01293) (SEQ ID NO: 21 and 22); protease A-2 (derived from NCIB12513, Patent Publication WO98/56927) (SEQ ID NO: 23); mutant proteases described in Japanese Patent Application Laid-Open (kokai) Nos. 2002-218989 and 2002-306176; mutants obtained through substitution of position 251 of the amino acid sequence of SEQ ID NO: 1 by asparagine, threonine, isoleucine, valine, leucine or glutamine; mutants obtained through substitution of position 256 of the same amino acid sequence by serine, glutamine, asparagine, valine, or alanine (Japanese Patent Application Laid-Open (kokai) No. 2003-125783); a mutant obtained through substitution of position 65 of the amino acid sequence of SEQ ID NO: 1 by proline; a mutant obtained through substitution of position 101 of the same amino acid sequence by asparagine; mutants obtained through substitution of position 273 of the same amino acid sequence by isoleucine, glycine, or threonine; mutants obtained through substitution of position 320 of the same amino acid sequence by phenylalanine, valine, threonine, leucine, isoleucine, or glycine; mutants obtained through substitution of position 359 of the same amino acid sequence by serine, leucine, valine, isoleucine, or glutamine, mutants obtained through substitution of position 387 of the same amino acid sequence by alanine, lysine, glutamine, glutamic acid, arginine, or histidine (Japanese Patent Application Laid-Open (kokai) No. 2004-000122); mutants obtained through substitution of position 163 of the amino acid sequence of SEQ ID NO: 1 by histidine, aspartic acid, phenylalanine, lysine, asparagine, serine, isoleucine, leucine, glutamine, threonine or valine; mutants obtained through substitution of position 170 of the same amino acid sequence by valine or leucine; mutants obtained through substitution of position 171 of the same amino acid sequence by alanine, glutamic acid, glycine, or threonine (Japanese Patent Application Laid-Open (kokai) No. 2004-057195); and an alkaline protease having an amino acid sequence that exhibits a 80% or higher, preferably 87% or more, more preferably 90% or more, still more preferably 95% or more, homology with any of the above listed amino acid sequences.

Homology of amino acid sequences can be preferably determined by the Lipman-Pearson method (Science, 227, 1435, 1985).

"Amino acid residues located at positions corresponding to the positions . . . " can be identified by comparing amino acid sequences of alkaline proteases by means of a known algorithm such as the Lipman-Pearson method, to thereby assign maximum homology to conserved amino acid residues present in the amino acid sequences. When the amino acid sequences of proteases are aligned by means of such method, regardless of insertion or deletion occurred in the amino acid sequences, the positions of the homologous amino acid residues can be determined in each of the proteases. Conceivably, homologous amino acid residues are located at the same positions in the three-dimensional structure of protease, whereby analogous effects are obtained in terms of specific functions of the intended protease.

As shown in FIG. 1, in which amino acid sequences are aligned by means of the aforementioned method, the amino acid residue at "(a) position 63 of the amino acid sequence of SEQ ID NO: 1" is asparagine. Through use of the method described in the above paragraph, an amino acid residue at a position corresponding to that position can be identified as, for example, asparagine at position 63 in case of protease KP9860. In this connection, the amino acid residue at that position is preferably serine.

The amino acid residue at "(b) position 89 of the amino acid sequence of SEQ ID NO: 1" is glutamine. Through use of the above-described method, an amino acid residue at a position corresponding to that position can be identified as, for example, glutamine at position 88 in case of protease E-1. Preferably, the amino acid residue at that position is histidine.

The amino acid residue at "(c) position 120 of the amino acid sequence of SEQ ID NO: 1" is serine. Through use of the above-described method, an amino acid residue at a position corresponding to that position can be identified as, for example, serine at position 119 in case of protease A-2. Preferably, the amino acid residue at that position is arginine.

The amino acid residues at "1(d) positions 63 and 187 of the amino acid sequence of SEQ ID NO: 1" are both asparagine. Through use of the above-described method, amino acid residues at positions corresponding to those positions can be identified as, for example, asparagines at positions 63 and 186 in case of protease SD-521. Preferably, both of the amino acid residues at those positions are serine.

The amino acid residue at "(e) position 226 of the amino acid sequence of SEQ ID NO: 1" is phenylalanine. Through use of the above-described method, an amino acid residue at a position corresponding to that position can be identified as, for example, phenylalanine at position 225 in case of protease Ya. Preferably, the amino acid residue at that position is tyrosine.

The amino acid residue at "(f) position 296 of the amino acid sequence of SEQ ID NO: 1" is isoleucine. Through use of the above-described method, an amino acid residue at a position corresponding to that position can be identified as, for example, isoleucine at position 296 in case of protease 9865. Preferably, the amino acid residue at that position is valine.

The amino acid residue at "(g) position 304 of the amino acid sequence of SEQ ID NO: 1" is asparagine. Through use of the above-described method, an amino acid residue at a position corresponding to that position can be identified as, for example, aspartic acid at position 303 in case of protease E-1. Preferably, the amino acid residue at that position is serine.

Specific examples of the positions and amino acid residues corresponding to (a) position 63, (b) position 89, (c) position 120, (d) positions 63 and 187, (e) position 226, (f) position 296, and (g) position 304 of the amino acid sequence (SEQ ID NO: 1) of protease KP43, are shown below by way of some preferred examples of the aforementioned "another alkaline protease" (Table 1).

protease) is replaced by another amino acid residue, the alkaline protease of the present invention can be obtained.

The alkaline protease of the present invention may be obtained through, for example, the following steps. Briefly, a cloned gene encoding parent alkaline protease (SEQ ID NO: 2; a gene encoding SEQ ID NO: 1, or a mature enzyme region, is represented by the sequence starting from the 619th codon) is mutated, and by use of the thus-mutated gene an appropriate host bacterium is transformed, followed by culturing of the recombinant host bacterium and collecting the alkaline protease product of the invention from the culture. Cloning of the gene encoding the parent alkaline protease may be carried out through a generally employed gene recombination technique. For example, a method described in Patent Publication WO99/18218 or Patent Publication WO98/56927 may be employed.

Means for carrying out mutagenesis of the gene encoding the parent alkaline protease may be random mutagenesis or site-directed mutagenesis which is commonly performed. More specifically, mutagenesis of the gene may be carried out by use of, for example, a Site-Directed Mutagenesis System Mutan-Super Express Km kit (Takara). Alternatively, by means of recombinant PCR (polymerase chain reaction; see

TABLE 1

| Position | Protease | | | | | | | |
|---|---|---|---|---|---|---|---|---|
| | KP43 | KP9860 | 9865 | E-1 | Ya | SD-521 | A-1 | A-2 |
| (a) | Asn63 | Asn63 | Asn63 | Asn63 | Ser63 | Asn63 | Asn63 | Asn63 |
| (b) | Gln89 | Gln89 | Gln89 | Gln88 | Gln88 | Gln88 | Gln89 | Gln88 |
| (c) | Ser120 | Ser120 | Ser120 | Asn119 | Asn119 | Asn119 | Ser120 | Ser119 |
| (d) | Asn63 | Asn63 | Asn63 | Asn63 | Ser63 | Asn63 | Asn63 | Asn63 |
| | Asn187 | Asn187 | Asn187 | Asn186 | Asn186 | Asn186 | Asn187 | Asn186 |
| (e) | Phe226 | Tyr226 | Phe226 | Phe225 | Phe225 | Phe225 | Phe226 | Tyr225 |
| (f) | Ile296 | Val296 | Ile296 | Val295 | Val295 | Val295 | Ile296 | Val295 |
| (g) | Asn304 | Asn304 | Asn304 | Asp303 | Asp303 | Asp303 | Asn304 | Asn303 |

Among the positions (a) to (g) of the amino acid residues of the alkaline protease of the present invention, two or more positions may be concurrently selected, so long as enzyme activity and enzyme characteristics remain unchanged. Preferred examples of two or more positions being selected concurrently are shown below. Amino acids are designated by the three letter codes, and the symbol "+" means an additional substitution.

Specific examples of double substitution of amino acid residues include Asn63Ser+Asn187Ser, Asn63Ser+Ile296Val, Asn187Ser+Ile296Val, and Ser120Arg+Phe226Tyr, wherein Asn63Ser+Asn187Ser is particularly preferred. Combinations of three or more substitutions may also be employed.

When the alkaline protease of the present invention is a mutant, the alkaline protease before undergoing mutagenesis (which may be referred to as "parent alkaline protease") is either a "protease having an amino acid sequence of SEQ ID NO: 1" or the aforementioned "another alkaline protease." When the parent alkaline protease is subjected to mutation at a predetermined site thereof, the alkaline protease of the present invention can be obtained. For example, when an amino acid residue at a position selected from among the aforementioned positions (a) to (g) of the amino acid sequence of SEQ ID NO: 1 of protease KP43 (or an amino acid residue at a position corresponding to any of the above positions in the amino acid sequence of another alkaline "PCR Protocols," Academic Press, New York, 1990), an arbitrary sequence of the gene can be replaced by the arbitrary sequence of another gene.

Production of the protease of the present invention by use of the thus-obtained mutant gene may be carried out, for example, by ligating the mutated gene to a DNA vector capable of stably amplifying the gene, to thereby transform host bacteria. Alternatively, the mutant gene may be introduced into chromosomal DNA of a host bacterium capable of stably maintaining the gene. Examples of the host bacterium which satisfies these requirements include bacteria belonging to the genus *Bacillus, Escherichia coli,* mold, yeast, and actinomycetes. Any of these microorganisms is inoculated into a culture medium containing an assimilable carbon source, nitrogen source, and other essential nutrients, and culturing is carried out according to a customary method.

From the thus-obtained culture, alkaline protease may be collected and purified by means of customary methods for collecting and purifying enzymes. For example, the culture is subjected to centrifugation or filtration to thereby remove cells, and the enzyme of interest is obtained from the culture supernatant by means of a routine purification technique. The thus-obtained enzyme solution may be employed as is. Alternatively, the enzyme solution may further be subjected to purification, crystallization, powdering, or granulation, any of which may be carried out according to a known method.

The thus-produced alkaline protease of the present invention exhibits oxidant resistance and maintains casein-degrading activity even in the presence of a fatty acid at a high concentration. The alkaline protease has a molecular weight of 43,000±2,000 as determined by SDS-PAGE, and is active within the alkaline region. Moreover, the alkaline protease exhibits a newly acquired property; i.e., improved thermal stability compared with that of the parent alkaline protease.

Thus, the alkaline protease of the present invention is useful as an enzyme to be incorporated in a variety of detergent compositions.

No particular limitation is imposed on the amount of the protease of the present invention to be incorporated into a detergent composition, so long as the alkaline protease exhibits its activity. The preferred amount is 0.1 to 5,000 PU per kg of detergent composition, more preferably 500 PU or less, in consideration of cost and other factors.

The detergent composition of the present invention may further contain a variety of enzymes in addition to the protease of the present invention. Examples of such additional enzymes include hydrolase, oxidase, reductase, transferase, lyase, isomerase, ligase, and synthetase. Of these, preferred enzymes include proteases other than those of the present invention, cellulase, keratinase, esterase, cutinase, amylase, lipase, pullulanase, pectinase, mannanase, glucosidase, glucanase, cholesteroloxidase, peroxidase, and laccase, among which the proteases, cellulase, amylase, and lipase are more preferred. Examples of the proteases include commercially available ones that are derived from *Bacillus* such as ALCALASE, ESPARASE, SAVINASE, EVERLASE, and KANNASE (all are registered trademarks; Novozymes), PROPARASE and PURAFECT (registered trademarks; Genencor); and KAP (Kao Corp.). Examples of cellulase include those derived from *Humicola* such as CELLUZYME and CAREZYME (registered trademarks; Novozymes); and KAC, alkaline cellulase produced by *Bacillus* sp. KSM-S237 disclosed in Japanese Patent Application Laid-Open (kokai) No. 10-313859, and mutated alkaline cellulase disclosed in Japanese Patent Application Laid-Open (kokai) No. 2003-313592 (these are products of Kao Corp.). Examples of amylase include those derived from *Bacillus* such as TERMARMYL and DURAMYL (registered trademarks; Novozymes), PURASTAR (registered trademark; Genencor), and KAM (Kao Corp.). Examples of lipase are those derived from *Thermomyces* and include LIPOLASE and LIPOLASE ULTRA (registered trademarks; Novozymes).

When a protease species other than the protease of the present invention is incorporated into a detergent composition together with the protease of the present invention, its amount is preferably 0.1 to 500 PU per kg of detergent composition. When cellulase is incorporated in combination, the amount of cellulase is preferably 300 to 3,000,000 KU per kg of detergent composition, based on the unit (KU) determined through the enzyme activity determination method described in paragraph [0020] of Japanese Patent Application Laid-Open (kokai) No. 10-313859.

When amylase is incorporated in combination, its amount is preferably 50 to 500,000 IU per kg of detergent composition based on the unit (IU) determined through the amylase activity determination method described in paragraph [0040] of Japanese Patent Application Laid-Open (kokai) No. 11-43690.

Moreover, when lipase is incorporated in combination, its amount is preferably 10,000 to 1,000,000 LU per kg of detergent composition based on the unit (LU) determined through the lipase activity determination method described in Example 1 of Japanese Kohyo (PCT) Patent Publication No. 8-500013.

Known detergent components may be incorporated into the detergent composition of the present invention. Examples of such known detergent components include the following substances.

(1) Surfactant

Generally, a surfactant is incorporated into the detergent composition in an amount of 0.5 to 60 mass%. In particular, the amount of surfactant is preferably 10 to 45 mass% for preparing a powdery detergent composition, and 20 to 50 mass% for preparing a liquid detergent composition. When the detergent composition of the present invention serves as a bleach composition or a detergent composition for an automated dishwasher, a surfactant is typically incorporated in an amount of 1 to 10 mass%, preferably 1 to 5 mass %.

Examples of the surfactant employed in the detergent composition of the present invention include an anionic surfactant, a nonionic surfactant, an amphoteric surfactant, a cationic surfactant, and a combination thereof. Of these, an anionic surfactant and a nonionic surfactant are preferred.

Examples of a preferred anionic surfactant include a sulfate ester salt of C10-C18 alcohol, a sulfate ester salt of an alkoxylated product of C8-C20 alcohol, an alkylbenzenesulfonate salt, a paraffinsulfonate salt, an α-olefinsulfonate salt, an α-sulfo fatty acid salt, and an α-sulfo fatty acid alkyl ester salt or a fatty acid salt. In the present invention, a linear C10-C14 (preferably C12-C14) alkylbenzenesulfonic acid salt is more preferred. The counter ion is preferably an alkali metal or an amine, and sodium and/or potassium, monoethanol amine, or diethanol amine is more preferred.

Examples of a preferred nonionic surfactant include a polyoxyalkylene alkyl (C8-C20) ether, an alkylpolyglycoside, a polyoxyalkylene alkyl (C8-C20) phenyl ether, a polyoxyalkylene sorbitan fatty acid (C8-C22) ester, a polyoxyalkylene glycol fatty acid (C8-C22) ester, and a polyoxyethylene polyoxypropylene block polymer. A more preferred nonionic surfactant is a polyoxyalkylene alkyl ether [having an HLB value (as calculated through the Griffin method) of 10.5 to 15.0, preferably 11.0 to 14.5] which is obtained by adding 4 to 20 moles of alkyleneoxide (e.g., ethyleneoxide and propyleneoxide) to a C10-C18 alcohol.

(2) Divalent Metal Ion Scavenger

A divalent metal ion scavenger is preferably incorporated into the composition in an amount of 0.01 to 50 mass %, preferably 5 to 40 mass %. Examples of the divalent metal ion scavenger to be employed in the detergent composition of the present invention include a condensed phosphate such as a tripolyphosphate, pyrophosphate, or orthophosphate; an aluminosilicate such as zeolite; a synthesized layered crystalline silicate; a nitrilotriacetate; an ethylenediamineteraacetate; a citrate; an isocitrate; and a polyacetalcarboxylate. Of these, a crystalline aluminosilicate (synthesized zeolite) is preferred. Among A-type, X-type, and P-type zeolites, A-type zeolite is more preferred. The synthesized zeolite preferably has an average primary particle size of 0.1 to 10 μm, more preferably 0.1 to 5 μm.

(3) Alkaline Agent

An alkaline agent is preferably incorporated into the composition in an amount of 0.01 to 80 mass %, preferably 1 to 40 mass %. Examples of the alkaline agent which may be incorporated into the detergent in powder form include an alkali metal carbonate such as sodium carbonate (collectively referred to as dense ash or light ash) and an amorphous alkali metal silicate such as JIS No. 1, No. 2, or No. 3. These inorganic alkaline agents are effective for the formation of the skeleton of particles during drying of the detergent, contributing to production of a detergent of relatively hard particles with excellent flowability. Examples of alkaline agents other than the above-described substances include sodium sesquicarbonate and sodium hydrogencarbonate. A phosphate such as tripolyphosphate also acts as an alkaline agent. Examples of alkaline agents to be employed in a detergent in liquid form include, in addition to the above-described alkaline agents, sodium hydroxide and mono-, di-, or tri-ethanol amine, which can also be employed as a counter ion of a surfactant.

(4) Anti-redeposition Agent

An anti-redeposition agent is preferably incorporated into the composition in an amount of 0.001 to 10 mass %, preferably 1 to 5 mass %. Examples of the anti-redeposition agent to be employed in the detergent composition of the present invention include a polyethylene glycol, a carboxylic polymer, a polyvinyl alcohol, and a polyvinyl pyrrolidone. Of these, the carboxylic polymer exerts not only an anti-redeposition effect, but also the effect of scavenging metal ions and the effect of releasing solid soil particles from the clothing into the washing liquid. The carboxylic polymer is a homopolymer or a copolymer of, for example, acrylic acid, methacrylic acid, or itaconic acid. Examples of preferred copolymers include a copolymerized product of any of the above monomers and maleic acid. The copolymer preferably has a molecular weight of some thousands to 100,000. In addition to the above carboxylic polymers, a polymer such as poly(glycidyl acid salt), a cellulose derivative such as carboxymethyl cellulose, and an aminocarboxylic polymer such as poly(aspartic acid) are also preferred, since these substances function as a metal ion scavenger, a dispersing agent, and an anti-redeposition agent.

(5) Bleaching Agent

A bleaching agent such as hydrogen peroxide or a percarbonate is incorporated into the composition, preferably in an amount of 1 to 10 mass %. When such a bleaching agent is employed, tetraacetylethylenediamine (TAED) or a bleaching activator described in, for example, Japanese Patent Application Laid-Open (kokai) No. 6-316700 may be incorporated into the composition in an amount of 0.01 to 10 mass %.

(6) Fluorescent Agent

Examples of a fluorescent agent which may be incorporated into the detergent composition of the present invention include a biphenyl fluorescent agent (e.g., Tinopal CBS-X) and a stilbene fluorescent agent (e.g., DM-type fluorescent agent). The fluorescent agent is preferably incorporated in an amount of 0.001 to 2 mass %.

(7) Other Components

The detergent composition of the present invention may contain a builder, a softener, a reducing agent (e.g., sulfite), a deformer (e.g., silicone), a perfume, or other additives, which are known in the field of laundry detergents.

The detergent composition of the present invention can be produced through a routine method by using, in combination, the protease product of the present invention obtained through the above-described method and known detergent components as listed above. The form of the detergent may be determined in accordance with its use, and examples of the form include liquid, powder, granules, paste, and solid.

The thus-obtained detergent composition of the present invention can be used as, among others, a laundry detergent, a bleaching agent, a detergent for hard surfaces, a drainpipe detergent, a denture detergent, or a germicidal detergent for medical instruments.

EXAMPLES

The following examples further describe and demonstrate embodiments of the present invention. The examples are given solely for the purpose of illustration and are not to be construed as limitations of the present invention.

Example 1

Phe46Leu, Tyr195Gly, and Phe46Leu+Tyr195Gly, which are mutants of an alkaline protease derived from *Bacillus* sp. KSM-KP43, are all known to be very effective in improving specific activity (Japanese Patent Application Laid-Open (kokai) No. 2002-218989). When these specific activity-improved mutants were treated at 70° C. for 15 minutes, their residual activity was found to drop to as low as 5 to 25%, as contrasted to the residual activity of the parent alkaline protease which maintained 70 to 80% of the activity before treatment. Therefore, each of these mutants was subjected to random mutagenesis of gene for producing a mutant exhibiting improved thermal stability. Briefly, a structural gene of the mutant having a size of about 2 kb was inserted into pKF18k (Takara) so as to serve as a template DNA (30 ng). PCR was performed by use of the thus-prepared template together with Taq polymerase (2.5 U), BcaBEST Sequencing Primer RV-M and BcaBEST Sequencing Primer M13-47 (both are products of Takara; 20 pmol each), dNTP (20 pmol), Takara Taq-added reaction buffer, and appropriate amounts of manganese sulfate and dimethyl sulfoxide. In PCR, the template DNA was denatured at 94° C. for one minute, followed by 30 cycles of treatment, each cycle consisting of 94° C.×one minute, 55° C.×two minutes, and 72° C.×three minutes. The resultant PCR product was left to stand at 72° C. for 10 minutes.

The PCR product was purified by use of a High Pure PCR Product Purification kit (Roche), and eluted with sterile water (100 µL). The thus-obtained DNA fragment of about 2 kb was cleaved by BamHI and XbaI (Roche), and then mixed with pKF18k which had been treated with the same enzyme. Ligation was allowed to proceed at 16° C. for 12 hours by use of a DNA Ligation kit (ver. 2; Takara). DNA was recovered through ethanol precipitation of a reaction mixture, whereby *Escherichia coli* HB101 strains were transformed. The transformants were grown on an LB agar medium containing skim milk and kanamycin.

Transformants showing resistance to kanamycin and giving translucent plaques around colonies by degrading of the skim milk were selected and inoculated into an LB culture medium containing skim milk and kanamycin, followed by shaking of the culture at 30° C. for 72 hours. The activity of culture supernatant was measured through the synthetic substrate method, which will be described hereinbelow. Measurement was performed for a supernatant system which had undergone a treatment of 70° C. for 15 minutes and a supernatant system wherein no treatment was performed, whereby residual activity after heat treatment was investigated. Mutants which was were increased by about 10% to about 50% in thermal stability compared with the level shown by the parent protease were subjected to colony PCR for gene amplification, then to purification, followed by nucleotide sequencing with a DNA Sequencer (model: 377, Applied Biosystems) employing a Big Dye DNA sequencing kit (Applied Biosystems). The above process gave the following thermal-stability-improved mutants. They are a mutant in which asparagine at position 63 was replaced by serine, a mutant in which glutamine at position 89 was replaced by histidine, a mutant in which serine at position 120 was replaced by arginine, a mutant in which asparagine at position 187 was replaced by serine, a mutant in which phenylalanine at position 226 was replaced by tyrosine, a mutant in which isoleucine at position 296 was replaced by valine, a mutant in which asparagine at position 304 was replaced by serine, and a mutant in which asparagines at positions 63 and 187 were both replaced by serines.

Example 2

The points of mutation that were found to be effective for enhancing thermal stability in Example 1 were individually introduced to protease KP43 of SEQ ID NO: 1, followed by site-directed-mutagenesis for evaluation of thermal stability.

A template plasmid for mutagenesis was constructed by introducing, into BamHI- and XbaI-cleaved sites of a pKF18K's multicloning site, a gene (SEQ ID NO: 2) coding for protease KP43.

Takara LA Taq (Takara) was employed in PCR for site-directed mutagenesis. Mutagenesis PCR was carried out by use of a selection primer whose 5'-end had been phosphorylated (20 pmol; included in a Mutan Super Express Km kit), each of primers 1 to 7 (SEQ ID NOs: 4 to 10; primers for mutagenesis; 20 pmol), and a template plasmid (30 ng). Reaction conditions of PCR were as follows. Firstly, the template DNA was denatured at 94° C. for one minute, then 30 cycles of treatment, each cycle consisting of 94° C.×one minute, 55° C.×one minute, and 72° C.×four minutes, were performed. The resultant PCR fragments were purified and used as primers. By use of the primers, a template plasmid (30 ng) and LA Taq, another PCR was carried out. Reaction conditions of this PCR were as follows. Thirty cycles of treatment, each cycle consisting of 94° C.×one minute, 55° C.×two minutes, and 72° C.×four minutes, were performed. The resultant PCR product was purified and subjected to a ligation reaction. Subsequently, *Escherichia coli* MV1184 strains were transformed, whereby mutation-introduced plasmid was obtained. The nucleotide sequence of alkaline protease gene of the resultant plasmid was determined, and the sites of mutation were confirmed.

As representative examples of combinations of mutation, double mutants were created through PCR on the basis of the above-prepared mutants and primers 1 to 7.

In order to produce and evaluate mutation-introduced alkaline protease, *Bacillus* sp. KSM-9865 (FERM P-18566) and pHA64 (Japanese Patent Application Laid-Open (kokai) No. 2000-287687: having BamHI- and XbaI-cleaved sites downstream of promotor 64) were employed, since they were considered to serve as a suitable system for this purpose for the reason that pHA64 is capable of replicating in *Bacillus* bacteria. Each of the above-prepared mutation-introduced plasmids was treated with BamHI and XbaI, and then mixed with pHA64 which had been treated with the same enzymes. Ligation was performed through use of a DNA Ligation kit (ver. 2; Takara). The DNA product was recovered from the ligase reaction solution through ethanol precipitation and employed in the subsequent transformation step.

The strain KSM-9865 which had undergone the transformation step were grown on a skim milk-containing alkaline agar medium [skim milk (Difco) (1% (w/v)), bactotryptone (Difco) (1%), yeast extract (Difco) (0.5%), sodium chloride (1%), agar (1.5%), sodium carbonate (0.05%), and tetracycline (15 ppm)]. Whether or not a mutated protease gene had been introduced to the strain KSM-9865 was determined on the basis of halo formation. The resultant transformants were inoculated into a seed culture medium (5 mL) [6.0% (w/v) polypeptone S, 0.05% of yeast extract, 1.0% of maltose, 0.02% of magnesium sulfate heptahydrate, 0.1% of potassium dihydrogenphosphate, 0.25% of sodium carbonate, and 30 ppm of tetracycline], followed by shaking of the culture for 16 hours at 30° C. The seed culture broth (1% (v/v)) was inoculated into a main culture medium (30 mL) [8% of polypeptone S, 0.3% of yeast extract, 10% of maltose, 0.04% of magnesium sulfate heptahydrate, 0.2% of potassium dihydrogenphosphate, 1.5% of sodium carbonate anhydrate, and 30 ppm of tetracycline], followed by shaking of the culture for three days at 30° C.

Example 3

Figure 3:
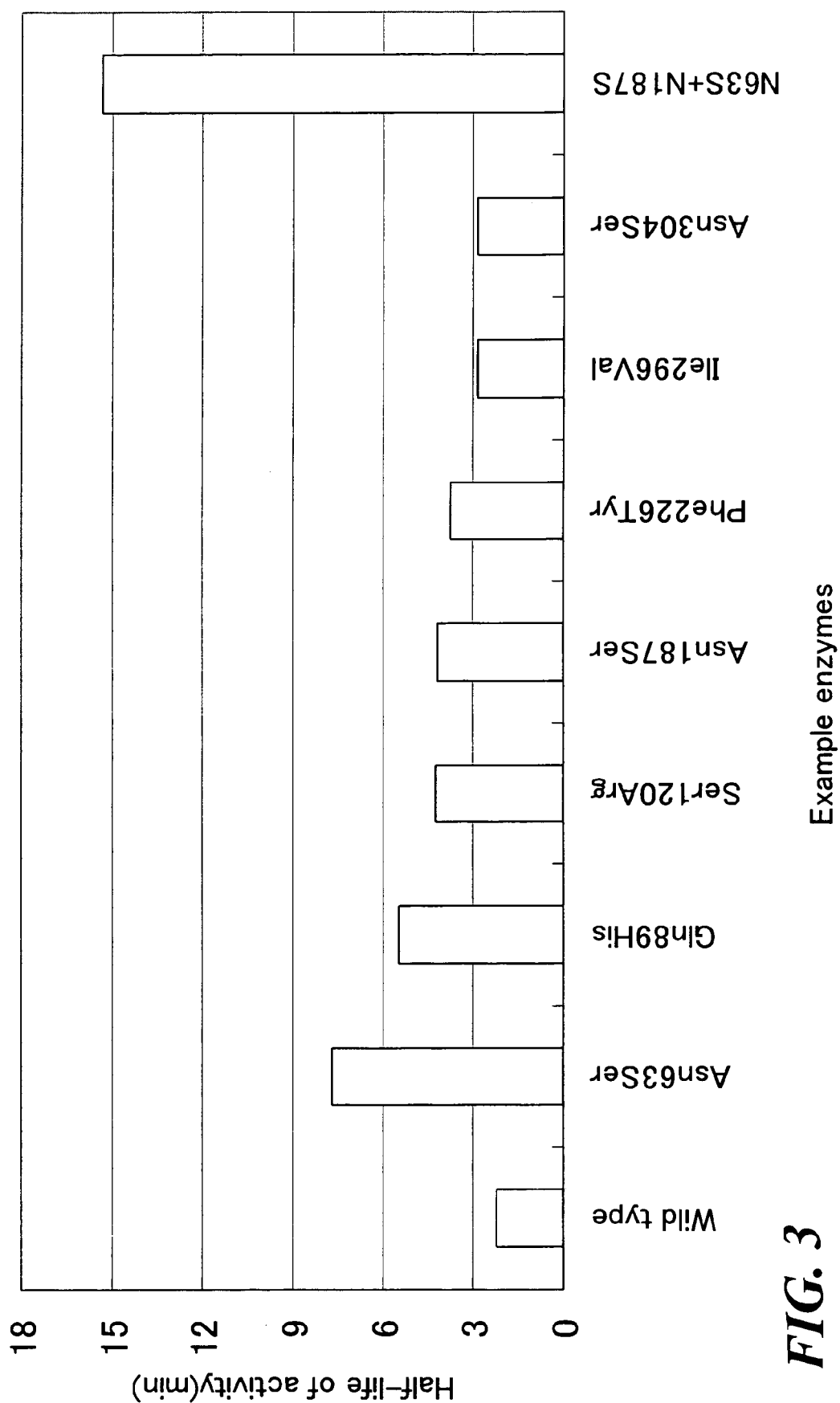

Each of the culture supernatants was treated at 60 to 80° C. for 10 minutes in 50 mM borate buffer (pH 10.5: with or without 2 mM calcium chloride), 50 mM Tris-HCl buffer (pH 7: with 2 mM calcium chloride), or a 2 mM aqueous calcium chloride solution. The residual activity each of the culture supernatants was determined through the casein method, and the ratio of the residual activity to that before heat treatment was calculated. All the mutants were found to have a higher residual activity ratio as compared with the parent alkaline protease treated under the same conditions, confirming improvement in thermal stability. Some of the results are shown in FIGS. 2 and 3. These figures show the half-life period (period of time elapsed until the residual activity drops to 50% of the initial residual activity) of the proteases maintained at a certain constant temperature. As is clear from FIGS. 2 and 3, each mutant exhibited a half-value period 1.2 to 7 times that of the parent alkaline protease.

The alkaline protease mutants produced through the above process were found to exhibit enhanced thermal stability. Except for this new characteristic, they were found to maintain the characteristics of the parental alkaline protease; i.e., they exhibit oxidant resistance, maintain casein-degrading activity even in the presence of a fatty acid of high concentration, have a molecular weight of 43,000±2,000 as determined by SDS-PAGE, and are active within the alkaline region.

Referential Examples

<Protease Assay (Synthetic Substrate Method)>

To a 100 mM borate buffer (pH 10.5) containing 0.05 mL of a 6 mL synthetic substrate (Glt-Ala-Ala-Pro-Leu-pNA: (SEQ ID NO: 24): Peptide Institute), an enzyme solution (0.05 mL) was added, to thereby initiate reaction at 30° C. for 15 minutes in a microplate reader (iEMS reader MF: LAB-SYSTEMS). Increase in absorbance at 414 nm was employed as an activity index. One unit of protease activity was defined as the amount of enzyme required for increasing the absorbance by 0.001 per minute under the above reaction conditions.

<Protease Assay (Casein Method)>

A 50 mM borate buffer (pH 10.5) (1 mL) containing casein (Hammerstein method: Merck, 1% (w/v)) was maintained at 30° C. for five minutes, and subsequently an enzyme solution (0.1 mL) was added to the buffer, to thereby allow reaction to proceed for 15 minutes. A reaction stopping solution (0.11M trichloroacetic acid/0.22M sodium acetate/0.33M acetic acid) (2.0 mL) was added to the resultant reaction mixture, and the mixture was allowed to stand at room temperature for 30 minutes. Thereafter, the precipitation was subjected to filtration by use of a Whatman No. 1 filter, and the degradation product was quantified by means of the method described by Lowry, et al. Specifically, an alkaline copper solution (1%

Rochelle salt: 1% copper sulfate pentahydrate: 2% sodium carbonate/0.1N sodium hydroxide solution=1:1:100) (2.5 mL) was added to the filtrate (0.5 mL), and the resultant mixture was allowed to stand at 30° C. for 10 minutes. Subsequently, to the mixture was added a phenol reagent [obtained by diluting a commercial phenol reagent (Kanto Kagaku) two-fold with deionized water] (0.25 mL), and the resultant mixture was thoroughly stirred and left to stand at 30° C. for 30 minutes. Thereafter, the absorbance of the mixture was measured at 660 nm. One unit of protease activity (1 PU) was defined as the amount of enzyme required for producing acid-soluble protein equivalent to 1 mmol of tyrosine per minute under the above reaction conditions.

Example 4

(1) Preparation of Detergent

Water (465 kg) was added to a mixing bath (1 m³) equipped with a stirring paddle. After the temperature of the water reached 55° C., a 40% (w/v) sodium polyacrylate aqueous solution (135 kg) was added to the water. The resultant mixture was stirred for 15 minutes, and then sodium carbonate (120 kg), sodium sulfate (60 kg), sodium sulfite (9 kg), and a fluorescent dye (3 kg) were added to the mixture. The resultant mixture was further stirred for 15 minutes, zeolite (300 kg) was added to the mixture, followed by stirring for 30 minutes, to thereby yield a homogenous slurry (the water content of the slurry: 50 mass %). The slurry was sprayed through pressure spray nozzles provided in the vicinity of the top of a spray-drying tower, to thereby yield a granular base (a high-temperature gas was fed at 225° C. from a lower part of the spray-drying tower, and discharged at 105° C. from the top of the tower).

Subsequently, the thus-obtained granular base (100 parts by mass) was fed to a Lodige mixer (product of Matsuzaka Giken Co., Ltd., capacity: 20 L, equipped with a jacket). While the granular base was stirred by use of the main shaft (150 rpm), a mixture of a nonionic surfactant (20 parts by mass), sodium linear alkyl (C10-C13) benzenesulfonate (22 parts by mass), a fatty acid (C14-C18) sodium salt (4 parts by mass), polyethylene glycol (2 parts by mass), and water (4 parts by mass) was added to the mixer over three minutes. Thereafter, the resultant mixture was stirred for five minutes. Furthermore, crystalline sodium silicate (20 parts by mass) and zeolite (10 parts by mass) were added to the mixer for surface coating, to thereby yield a detergent base.

The detergent base (99 mass %) was mixed with example protease granules of the present invention (0.5 mass %) and a perfume (0.5 mass %), to thereby produce an end product, granular detergent A.

(2) Raw Materials Employed

Nonionic surfactant: Emulgen 108KM (average mole number of ethylene oxide added: 8.5, product of Kao Corporation)

Aqueous solution of sodium polyacrylate: average molecular weight: 10,000 (produced by use of the method described in the examples of Japanese Patent Publication (kokoku) No. 2-24283)

Sodium carbonate: Dense ash (product of Central Glass Co., Ltd.)

Zeolite: Zeolite 4A (average particle size: 3.5 µm, product of Tosoh Corporation)

Polyethylene glycol: K-PEG6000 (average molecular weight: 8,500, product of Kao Corporation)

Crystalline sodium silicate: Powder SKS-6 (product of Hoechst Tokuyama)

Example protease granules of the present invention: granules prepared from each of purified samples of the example alkaline proteases of the present invention shown in FIGS. 2 and 3 by the method described in Example 1 of Japanese Patent Application Laid-Open (kokai) No. 62-257990 (6 PU/g)

Fluorescent dye: Tinopal CBS-X (product of Ciba-Geigy Corp.)

Example 5

(1) Preparation of Detergent

The slurry (solid content: 50 mass %) was spray-dried with hot air at 250° C., to thereby yield a granular base containing sodium polyacrylate (mass average molecular weight: 10,000) (7 mass %), sodium carbonate (26 mass %), sodium sulfate (20 mass %), sodium chloride (6 mass %), fluorescent dye (0.5 mass %), zeolite (40 mass %), and water (0.5 mass %).

Subsequently, the thus-obtained granular base (100 parts by mass) was fed to a Lodige mixer (product of Matsuzaka Giken Co., Ltd., capacity: 20 L, equipped with a jacket). While the granular base was stirred by means of the main shaft (150 rpm), a mixture of a nonionic surfactant (20 parts by mass), sodium linear alkyl (C10-C13) benzenesulfonate (22 parts by mass), a fatty acid (C14-C18) sodium salt (4 parts by mass), polyethylene glycol (2 parts by mass), and water (4 parts by mass) was added to the mixer over three minutes. Thereafter, the resultant mixture was stirred for five minutes. Furthermore, crystalline sodium silicate (20 parts by mass) and zeolite (10 parts by mass) were added to the mixer for surface coating, to thereby yield a detergent base.

The detergent base (95 mass %) was mixed with bleaching agent granules (2.8 mass %), bleaching activator granules (1.2 mass %), example protease granules of the present invention (0.5 mass %), and a perfume (0.5 mass %), to thereby produce an end product, granular detergent B.

(2) Raw Materials Employed

Nonionic surfactant: Emulgen 108KM (average mole number of ethylene oxide added: 8.5, product of Kao Corporation)

Aqueous solution of sodium polyacrylate: average molecular weight: 10,000 (produced by the method described in the examples of Japanese Patent Publication (kokoku) No. 2-24283)

Sodium carbonate: Dense ash (product of Central Glass Co., Ltd.)

Zeolite: Zeolite 4A (average particle size: 3.5 µm, product of Tosoh Corporation)

Polyethylene glycol: K-PEG6000 (average molecular weight: 8,500, product of Kao Corporation)

Crystalline sodium silicate: SKS-6 (product of Hoechst Tokuyama)

Example Protease granules of the present invention: granules prepared from each of the purified samples of the example alkaline proteases of the present invention shown in FIGS. 2 and 3 by the method described in Example 1 of Japanese Patent Application Laid-Open (kokai) No. 62-257990 (6 PU/g)

Fluorescent dye: Tinopal CBS-X (product of Ciba-Geigy Corp.)

Bleaching agent granules: a sodium carbonate-hydrogen peroxide addition product (produced in a manner similar to that for producing bleaching agent granules described in paragraph [0019] of Japanese Patent Application Laid-Open (kokai) No. 2000-256699)

Bleaching activator granules: granules of sodium lauroyloxybenzenesulfonate (produced in a manner similar to that for producing bleaching activator granules described in paragraph [0018] of Japanese Patent Application Laid-Open (kokai) No. 2000-256699)

Example 6

Liquid detergent compositions (detergents C and D) shown in Table 2 were prepared.

TABLE 2

| Components | Detergent C (mass %) | Detergent D (mass %) |
|---|---|---|
| Nonionic surfactant[1] | 25.0 | — |
| Nonionic surfactant[2] | 5.0 | — |
| Nonionic surfactant[3] | 10.0 | — |
| Nonionic surfactant[4] | — | 9.0 |
| Nonionic surfactant[5] | — | 9.0 |
| Nonionic surfactant[6] | — | 2.5 |
| Anionic surfactant[7] | 1.0 | — |
| Silicone[8] | — | 0.8 |
| Carboxylic acid-based polymer[9] | 2.0 | — |
| Polymer[10] | — | 0.8 |
| Citric acid | 0.2 | — |
| Calcium chloride | 0.05 | — |
| Monoethanolamine | 4.0 | — |
| Triethylene glycol phenyl ether | 3.0 | — |
| Propylene glycol | 3.0 | — |
| Ethanol | 2.0 | 2.0 |
| Sodium sulfite | 0.2 | — |
| Example Protease of the present invention[11] | 0.5 | 1.0 |
| Perfume | 0.5 | 0.5 |
| Water | Balance | Balance |
| Total | 100 | 100 |
| Concentration upon use | 20 g/30 L | 40 g/30 L |
| pH of detergent solution | 10.5 | 7.3 |

[1]Polyoxyethylene (average mole number added: 7) alkyl ether having an alkyl group derived from a C12-C14 secondary alcohol (Softanol 70, product of Nippon Shokubai Kagaku Kogyo)
[2]Polyoxyethylene (average mole number added: 12) alkyl ether having an alkyl group derived from a C12-C14 secondary alcohol (Softanol 120, product of Nippon Shokubai Kagaku Kogyo)
[3]A product obtained by sequential block addition of EO (average mole number: 5), PO (average mole number: 2), and EO (average mole number: 3) to a C10-C14 linear primary alcohol
[4]Polyoxyethylene lauryl ether (average mole number of EO added: 8)
[5]Polyoxyethylene lauryl ether (average mole number of EO added: 11.5)
[6]Narrow range polyoxyethylene alkyl (sec-$C_{12}/C_{13}$) ether
[7]Sodium linear alkyl (C10-C14) benzenesulfonate
[8]Amide/ether-modified silicone polymer (BY16-906, product of Dow Corning Toray Silicone Co., Ltd.)
[9]A phenoxypolyethylene glycol - acrylic acid - maleic acid copolymer synthesized by the method described in lines 6 through 13 of page 11 of Japanese Patent Application Laid-Open (kokai) No. 10-60476 (mass average molecular weight: 10,000, solid content: 51.2%)
[10]A sodium salt of a pentene/maleic acid (ratio by mol: 50/50) copolymer (mass average molecular weight: 7,000)
[11]A purified sample of each of the example alkaline proteases of the present invention shown in FIGS. 2 and 3 (15 PU/mL)

Example 7

While sodium percarbonate and sodium carbonate (dense ash) of the components shown in Table 3 below were mixed while stirring, a 40% aqueous solution of sodium polyacrylate and sodium linear alkyl benzenesulfonate, or a nonionic surfactant, or sodium lauroyloxybenzenesulfonate were added to the mixture. Subsequently, to the resultant mixture were added example protease granules of the present invention prepared by the method described in Example 1 of Japanese Patent Application Laid-Open (kokai) No. 62-257990, and the resultant mixture was stirred until a uniform mixture was obtained to give a bleaching agent.

TABLE 3

| Components | Bleaching agent E (mass %) | Bleaching agent F (mass %) |
|---|---|---|
| Sodium percarbonate[1] | 72.0 | 72.0 |
| Sodium carbonate (dense ash) | 20.0 | 20.0 |
| Anionic surfactant[2] | 2.0 | — |
| Nonionic surfactant[3] | — | 2.0 |
| Sodium polyacrylate[4] | 1.0 | 1.0 |
| Sodium lauroyloxybenzenesulfonate | 4.0 | 4.0 |
| Example Protease of the present invention[5] | 1.0 | 1.0 |

[1]Particle size: 500 to 700 μm
[2]Sodium linear alkyl (C12-C14) benzenesulfonate
[3]Polyoxyethylene alkyl ether (number of carbon atoms of the alkyl group: 12 to 14, average mole number of EO added: 12)
[4]Average molecular weight: 8,000
[5]Granules (6 PU/g) prepared from each of purified samples of the alkaline proteases of embodiments of the present invention shown in FIGS. 2 and 3 by the method described in Example 1 of Japanese Patent Application Laid-Open (kokai) No. 62-257990

Example 8

Detergent compositions for an automatic dishwasher (detergents G and H) shown in Table 4 below were prepared.

TABLE 4

| Components | Detergent G (mass %) | Detergent H (mass %) |
|---|---|---|
| Pluronic L-61[1] | — | 4.0 |
| Softanol EP-7085[2] | 4.0 | — |
| Trisodium citrate | — | 30.0 |
| Sodium tripolyphosphate | 30.0 | — |
| Sodium percarbonate | 20.0 | 20.0 |
| Sodium carbonate | 20.0 | 20.0 |
| Amorphous silicate[3] | 10.0 | 10.0 |
| AA-MA[4] | 4.0 | 4.0 |
| Sodium sulfate | 10.0 | 10.0 |
| α-Amylase[5] | 1.0 | 1.0 |
| Example Protease of the present invention[6] | 1.0 | 1.0 |

[1]Polyoxyethylene - polyoxypropylene copolymer (average molecular weight: 2,000)
[2]A product obtained by adding to a C12-C14 sec-alcohol ethylene oxide (7 mol) and propylene oxide (8.5 mol)
[3]JIS No. 2 sodium silicate
[4]An acrylic acid - maleic acid copolymer
[5]DURAMYL 60T (registered trademark; an amylase derived from Bacillus which is a product of Novozymes)
[6]Granules (6 PU/g) prepared from each of purified samples of the alkaline proteases of the embodiments of the present invention shown in FIGS. 2 and 3 by the method described in Example 1 of Japanese Patent Application Laid-Open (kokai) No. 62-257990

Example 9

A detergent composition for hard surfaces (detergent J) was prepared from components shown in Table 5 below.

TABLE 5

| Components | Detergent J (mass %) |
|---|---|
| Anionic surfactant[1] | 15.0 |
| Nonionic surfactant[2] | 5.0 |
| Nonionic surfactant[3] | 5.0 |
| Amphoteric surfactant[4] | 7.5 |
| Amphoteric surfactant[5] | 4.0 |
| Citric acid | 1.0 |
| Polypropylene glycol[6] | 2.0 |

TABLE 5-continued

| Components | Detergent J (mass %) |
|---|---|
| Ethanol | 5.0 |
| Example Protease of the present invention[7] | 1.0 |
| Perfume, water, etc./pH modifier | 54.5 |
| Total | 100.0 |

[1] Sodium polyoxyethylene (EOP = 4) alkyl (C12) ether sulfate
[2] Polyoxyethylene (EOP = 8) alkyl (C12) ether
[3] Alkyl (C12) polyglucoside (condensation degree: 1.3)
[4] Mono long-chain tertiary alkyl (C12) dimethylamine oxide
[5] Alkyl (C12) hydroxydimethyl sulfobetaine
[6] Molecular weight: 10,000
[7] Each of the purified samples of the example alkaline protease of the present invention shown in FIGS. 2 and 3 (15 PU/mL)

Example 10

Granular detergents shown in Table 6 below were prepared by use of the aforementioned detergent A (see Example 2).

TABLE 6

| Components (mass %) | Detergent K | Detergent L | Detergent M | Detergent N |
|---|---|---|---|---|
| Detergent base of Example 2 | 98.4 | 98.3 | 98.5 | 97.2 |
| Perfume | 0.5 | 0.5 | 0.5 | 0.5 |
| Example Protease of the present invention[1] | 0.5 | 0.5 | 0.5 | 0.5 |
| Conventional protease[2] | 0.6 | | | 0.6 |
| Cellulase[3] | | 0.7 | | 0.7 |
| Lipase[4] | | | 0.5 | 0.5 |

[1] Granules (6 PU/g) prepared from each of purified samples of the example alkaline proteases of the present invention shown in Table 1 by the method described in Example 1 of Japanese Patent Application Laid-Open (kokai) No. 62-257990
[2] Protease K-16 described in Japanese Patent Application Laid-Open (kokai) No. 5-25492, the activity thereof having been regulated to 5 PU/g by the method described in Example 1 of Japanese Patent Application Laid-Open (kokai) No. 62-257990
[3] KAC-500 (registered trademark; a cellulase derived from *Humicola* which is a product of Kao Corporation)
[4] LIPOLASE 100T (registered trademark; a lipase derived from *Thermomyces* which is a product of Novozymes)

The present invention enables production of an alkaline protease which has for example, a high thermal stability, exhibits activity even in the presence of a fatty acid at a high concentration and excellent detergency against complex

---

The invention claimed is:

1. An isolated alkaline protease consisting of an amino acid sequence wherein one or more amino acid residues selected from those located at (a) position 63, (b) position 89, (c) position 120, (d) positions 63 and 187, (e) position 226, (f) position 296, (g) position 304 of the amino acid sequence of SEQ ID NO: 1 are the following amino acid residues, respectively: (a) serine, (b) histidine, (c) arginine, (d) serine, (e) tyrosine, (f) valine, and (g) serine, and wherein said isolated alkaline protease has alkaline protease activity.

2. An isolated alkaline protease consisting of the amino acid sequence of SEQ ID NO: 1 or an amino acid sequence that is at least 98.1% homologous to the amino acid sequence of SEQ ID NO: 1, wherein one or more amino acid residues selected from those located at (a) position 63, (b) position 89, (c) position 120, (d) positions 63 and 187, (e) position 226, (f) position 296, (g) position 304 of the amino acid sequence of SEQ ID NO:1, or at positions corresponding to these positions, are the following amino acid residues, respectively: (a) serine, (b) histidine, (c) arginine, (d) serine, (e) tyrosine, (f) valine, and (g) serine, and wherein said isolated alkaline protease has alkaline protease activity.

* * * * *

SEQUENCE LISTING

<160> NUMBER OF SEQ ID NOS: 23

<210> SEQ ID NO 1
<211> LENGTH: 434
<212> TYPE: PRT
<213> ORGANISM: Bacillus sp. KSM-KP43

<400> SEQUENCE: 1

```
Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Thr Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Thr Ile Leu Phe Ala Ala
145                 150                 155                 160
```

```
Gly Asn Glu Gly Pro Asn Gly Thr Ile Ser Ala Pro Gly Thr Ala
            165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
            195                 200                 205

Gly Pro Thr Lys Asp Gly Arg Ile Lys Pro Asp Val Met Ala Pro Gly
        210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
            275                 280                 285

Leu Ile Ala Gly Ala Ala Asp Ile Gly Leu Gly Tyr Pro Asn Gly Asn
        290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
        355                 360                 365

Asp Leu Val Ile Thr Ala Pro Asn Gly Thr Gln Tyr Val Gly Asn Asp
        370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn

<210> SEQ ID NO 2
<211> LENGTH: 1923
<212> TYPE: DNA
<213> ORGANISM: Bacillus sp. KSM-KP43
<220> FEATURE:
<221> NAME/KEY: CDS
<222> LOCATION: (1)..(1920)
<220> FEATURE:
<221> NAME/KEY: sig_peptide
<222> LOCATION: (1)..(618)
<220> FEATURE:
<221> NAME/KEY: mat_peptide
<222> LOCATION: (619)..()

<400> SEQUENCE: 2 atg aga aag aag aaa aag gtg ttt tta tct gtt tta tca gct gca        45
Met Arg Lys Lys Lys Lys Val Phe Leu Ser Val Leu Ser Ala Ala
    -205                -200                -195 gcg att ttg tcg act gtt gcg tta agt aat cca tct gca ggt ggt        90
Ala Ile Leu Ser Thr Val Ala Leu Ser Asn Pro Ser Ala Gly Gly
    -190                -185                -180 gca agg aat ttt gat ctg gat ttc aaa gga att cag aca aca act       135
```

-continued

```
Ala Arg Asn Phe Asp Leu Asp Phe Lys Gly Ile Gln Thr Thr Thr
-175            -170            -165 gat gct aaa ggt ttc tcc aag cag ggg cag act ggt gct gct gct       180
Asp Ala Lys Gly Phe Ser Lys Gln Gly Gln Thr Gly Ala Ala Ala
-160            -155            -150 ttt ctg gtg gaa tct gaa aat gtg aaa ctc cca aaa ggt ttg cag       225
Phe Leu Val Glu Ser Glu Asn Val Lys Leu Pro Lys Gly Leu Gln
-145            -140            -135 aag aag ctt gaa aca gtc ccg gca aat aat aaa ctc cat att atc       270
Lys Lys Leu Glu Thr Val Pro Ala Asn Asn Lys Leu His Ile Ile
-130            -125            -120 caa ttc aat gga cca att tta gaa gaa aca aaa cag cag ctg gaa       315
Gln Phe Asn Gly Pro Ile Leu Glu Glu Thr Lys Gln Gln Leu Glu
-115            -110            -105 aaa aca ggg gca aag att ctc gac tac ata cct gat tat gct tac att   363
Lys Thr Gly Ala Lys Ile Leu Asp Tyr Ile Pro Asp Tyr Ala Tyr Ile
-100            -95             -90 gtc gag tat gag ggc gat gtt aag tca gca aca agc acc att gag cac   411
Val Glu Tyr Glu Gly Asp Val Lys Ser Ala Thr Ser Thr Ile Glu His
-85             -80             -75             -70 gtg gaa tcc gtg gag cct tat ttg ccg ata tac aga ata gat ccc cag   459
Val Glu Ser Val Glu Pro Tyr Leu Pro Ile Tyr Arg Ile Asp Pro Gln
                -65             -60             -55 ctt ttc aca aaa ggg gca tca gag ctt gta aaa gca gtg gcg ctt gat   507
Leu Phe Thr Lys Gly Ala Ser Glu Leu Val Lys Ala Val Ala Leu Asp
            -50             -45             -40 aca aag cag aaa aat aaa gag gtg caa tta aga ggc atc gaa caa atc   555
Thr Lys Gln Lys Asn Lys Glu Val Gln Leu Arg Gly Ile Glu Gln Ile
        -35             -30             -25 gca caa ttc gca ata agc aat gat gtg cta tat att acg gca aag cct   603
Ala Gln Phe Ala Ile Ser Asn Asp Val Leu Tyr Ile Thr Ala Lys Pro
    -20             -15             -10 gag tat aag gtg atg aat gat gtt gcg cgt gga att gtc aaa gcg gat   651
Glu Tyr Lys Val Met Asn Asp Val Ala Arg Gly Ile Val Lys Ala Asp
-5              -1  1           5               10 gtg gct cag agc agc tac ggg ttg tat gga caa gga cag atc gta gcg   699
Val Ala Gln Ser Ser Tyr Gly Leu Tyr Gly Gln Gly Gln Ile Val Ala
            15              20              25 gtt gcc gat aca ggg ctt gat aca ggt cgc aat gac agt tcg atg cat   747
Val Ala Asp Thr Gly Leu Asp Thr Gly Arg Asn Asp Ser Ser Met His
        30              35              40 gaa gcc ttc cgc ggg aaa att act gca tta tat gca ttg gga cgg acg   795
Glu Ala Phe Arg Gly Lys Ile Thr Ala Leu Tyr Ala Leu Gly Arg Thr
    45              50              55 aat aat gcc aat gat acg aat ggt cat ggt acg cat gtg gct ggc tcc   843
Asn Asn Ala Asn Asp Thr Asn Gly His Gly Thr His Val Ala Gly Ser
60              65              70              75 gta tta gga aac ggc tcc act aat aaa gga atg gcg cct cag gcg aat   891
Val Leu Gly Asn Gly Ser Thr Asn Lys Gly Met Ala Pro Gln Ala Asn
            80              85              90 cta gtc ttc caa tct atc atg gat agc ggt ggg gga ctt gga gga cta   939
Leu Val Phe Gln Ser Ile Met Asp Ser Gly Gly Gly Leu Gly Gly Leu
        95              100             105 cct tcg aat ctg caa acc tta ttc agc caa gca tac agt gct ggt gcc   987
Pro Ser Asn Leu Gln Thr Leu Phe Ser Gln Ala Tyr Ser Ala Gly Ala
    110             115             120 aga att cat aca aac tcc tgg gga gca gca gtg aat ggg gct tac aca   1035
Arg Ile His Thr Asn Ser Trp Gly Ala Ala Val Asn Gly Ala Tyr Thr
125             130             135
```

```
aca gat tcc aga aat gtg gat gac tat gtg cgc aaa aat gat atg acg    1083
Thr Asp Ser Arg Asn Val Asp Asp Tyr Val Arg Lys Asn Asp Met Thr
140                 145                 150                 155 atc ctt ttc gct gcc ggg aat gaa gga ccg aac ggc gga acc atc agt    1131
Ile Leu Phe Ala Ala Gly Asn Glu Gly Pro Asn Gly Gly Thr Ile Ser
                160                 165                 170 gca cca ggc aca gct aaa aat gca ata aca gtc gga gct acg gaa aac    1179
Ala Pro Gly Thr Ala Lys Asn Ala Ile Thr Val Gly Ala Thr Glu Asn
175                 180                 185 ctc cgc cca agc ttt ggg tct tat gcg gac aat atc aac cat gtg gca    1227
Leu Arg Pro Ser Phe Gly Ser Tyr Ala Asp Asn Ile Asn His Val Ala
            190                 195                 200 cag ttc tct tca cgt gga ccg aca aag gat gga cgg atc aaa ccg gat    1275
Gln Phe Ser Ser Arg Gly Pro Thr Lys Asp Gly Arg Ile Lys Pro Asp
    205                 210                 215 gtc atg gca ccg gga acg ttc ata cta tca gca aga tct tct ctt gca    1323
Val Met Ala Pro Gly Thr Phe Ile Leu Ser Ala Arg Ser Ser Leu Ala
220                 225                 230                 235 ccg gat tcc tcc ttc tgg gcg aac cat gac agt aaa tat gca tac atg    1371
Pro Asp Ser Ser Phe Trp Ala Asn His Asp Ser Lys Tyr Ala Tyr Met
                240                 245                 250 ggt gga acg tcc atg gct aca ccg atc gtt gct gga aac gtg gca cag    1419
Gly Gly Thr Ser Met Ala Thr Pro Ile Val Ala Gly Asn Val Ala Gln
            255                 260                 265 ctt cgt gag cat ttt gtg aaa aac aga ggc atc aca cca aag cct tct    1467
Leu Arg Glu His Phe Val Lys Asn Arg Gly Ile Thr Pro Lys Pro Ser
    270                 275                 280 cta tta aaa gcg gca ctg att gcc ggt gca gct gac atc ggc ctt ggc    1515
Leu Leu Lys Ala Ala Leu Ile Ala Gly Ala Ala Asp Ile Gly Leu Gly
285                 290                 295 tac ccg aac ggt aac caa gga tgg gga cga gtg aca ttg gat aaa tcc    1563
Tyr Pro Asn Gly Asn Gln Gly Trp Gly Arg Val Thr Leu Asp Lys Ser
                300                 305                 310                 315 ctg aac gtt gcc tat gtg aac gag tcc agt tct cta tcc acc agc caa    1611
Leu Asn Val Ala Tyr Val Asn Glu Ser Ser Ser Leu Ser Thr Ser Gln
            320                 325                 330 aaa gcg acg tac tcg ttt act gct act gcc ggc aag cct ttg aaa atc    1659
Lys Ala Thr Tyr Ser Phe Thr Ala Thr Ala Gly Lys Pro Leu Lys Ile
    335                 340                 345 tcc ctg gta tgg tct gat gcc cct gcg agc aca act gct tcc gta acg    1707
Ser Leu Val Trp Ser Asp Ala Pro Ala Ser Thr Thr Ala Ser Val Thr
350                 355                 360 ctt gtc aat gat ctg gac ctt gtc att acc gct cca aat ggc aca cag    1755
Leu Val Asn Asp Leu Asp Leu Val Ile Thr Ala Pro Asn Gly Thr Gln
365                 370                 375 tat gta gga aat gac ttt act tcg cca tac aat gat aac tgg gat ggc    1803
Tyr Val Gly Asn Asp Phe Thr Ser Pro Tyr Asn Asp Asn Trp Asp Gly
380                 385                 390                 395 cgc aat aac gta gaa aat gta ttt att aat gca cca caa agc ggg acg    1851
Arg Asn Asn Val Glu Asn Val Phe Ile Asn Ala Pro Gln Ser Gly Thr
            400                 405                 410 tat aca att gag gta cag gct tat aac gta ccg gtt gga cca cag acc    1899
Tyr Thr Ile Glu Val Gln Ala Tyr Asn Val Pro Val Gly Pro Gln Thr
    415                 420                 425 ttc tcg ttg gca att gtg aat taa                                    1923
Phe Ser Leu Ala Ile Val Asn
                430
```

<210> SEQ ID NO 3
<211> LENGTH: 640

```
<212> TYPE: PRT
<213> ORGANISM: Bacillus sp. KSM-KP43

<400> SEQUENCE: 3

Met Arg Lys Lys Lys Lys Val Phe Leu Ser Val Leu Ser Ala Ala
    -205                -200                -195
Ala Ile Leu Ser Thr Val Ala Leu Ser Asn Pro Ser Ala Gly Gly
    -190                -185                -180
Ala Arg Asn Phe Asp Leu Asp Phe Lys Gly Ile Gln Thr Thr Thr
    -175                -170                -165
Asp Ala Lys Gly Phe Ser Lys Gln Gly Gln Thr Gly Ala Ala Ala
    -160                -155                -150
Phe Leu Val Glu Ser Glu Asn Val Lys Leu Pro Lys Gly Leu Gln
    -145                -140                -135
Lys Lys Leu Glu Thr Val Pro Ala Asn Asn Lys Leu His Ile Ile
    -130                -125                -120
Gln Phe Asn Gly Pro Ile Leu Glu Glu Thr Lys Gln Gln Leu Glu
    -115                -110                -105
Lys Thr Gly Ala Lys Ile Leu Asp Tyr Ile Pro Asp Tyr Ala Tyr Ile
    -100                 -95                 -90
Val Glu Tyr Glu Gly Asp Val Lys Ser Ala Thr Ser Thr Ile Glu His
-85                  -80                  -75                 -70
Val Glu Ser Val Glu Pro Tyr Leu Pro Ile Tyr Arg Ile Asp Pro Gln
                     -65                  -60                 -55
Leu Phe Thr Lys Gly Ala Ser Glu Leu Val Lys Ala Val Ala Leu Asp
                -50                  -45                 -40
Thr Lys Gln Lys Asn Lys Glu Val Gln Leu Arg Gly Ile Glu Gln Ile
        -35                  -30                 -25
Ala Gln Phe Ala Ile Ser Asn Asp Val Leu Tyr Ile Thr Ala Lys Pro
        -20                  -15                 -10
Glu Tyr Lys Val Met Asn Asp Val Ala Arg Gly Ile Val Lys Ala Asp
-5                   -1  1                 5                  10
Val Ala Gln Ser Ser Tyr Gly Leu Tyr Gly Gln Gly Gln Ile Val Ala
                 15                   20                  25
Val Ala Asp Thr Gly Leu Asp Thr Gly Arg Asn Asp Ser Ser Met His
                 30                   35                  40
Glu Ala Phe Arg Gly Lys Ile Thr Ala Leu Tyr Ala Leu Gly Arg Thr
                 45                   50                  55
Asn Asn Ala Asn Asp Thr Asn Gly His Gly Thr His Val Ala Gly Ser
60                   65                   70                  75
Val Leu Gly Asn Gly Ser Thr Asn Lys Gly Met Ala Pro Gln Ala Asn
                 80                   85                  90
Leu Val Phe Gln Ser Ile Met Asp Ser Gly Gly Gly Leu Gly Gly Leu
                 95                  100                 105
Pro Ser Asn Leu Gln Thr Leu Phe Ser Gln Ala Tyr Ser Ala Gly Ala
                110                  115                 120
Arg Ile His Thr Asn Ser Trp Gly Ala Ala Val Asn Gly Ala Tyr Thr
                125                  130                 135
Thr Asp Ser Arg Asn Val Asp Asp Tyr Val Arg Lys Asn Asp Met Thr
140                  145                  150                 155
Ile Leu Phe Ala Ala Gly Asn Glu Gly Pro Asn Gly Gly Thr Ile Ser
                160                  165                 170
Ala Pro Gly Thr Ala Lys Asn Ala Ile Thr Val Gly Ala Thr Glu Asn
                175                  180                 185
```

Leu Arg Pro Ser Phe Gly Ser Tyr Ala Asp Asn Ile Asn His Val Ala
            190                 195                 200

Gln Phe Ser Ser Arg Gly Pro Thr Lys Asp Gly Arg Ile Lys Pro Asp
        205                 210                 215

Val Met Ala Pro Gly Thr Phe Ile Leu Ser Ala Arg Ser Ser Leu Ala
220                 225                 230                 235

Pro Asp Ser Ser Phe Trp Ala Asn His Asp Ser Lys Tyr Ala Tyr Met
                240                 245                 250

Gly Gly Thr Ser Met Ala Thr Pro Ile Val Ala Gly Asn Val Ala Gln
                255                 260                 265

Leu Arg Glu His Phe Val Lys Asn Arg Gly Ile Thr Pro Lys Pro Ser
            270                 275                 280

Leu Leu Lys Ala Ala Leu Ile Ala Gly Ala Ala Asp Ile Gly Leu Gly
        285                 290                 295

Tyr Pro Asn Gly Asn Gln Gly Trp Gly Arg Val Thr Leu Asp Lys Ser
300                 305                 310                 315

Leu Asn Val Ala Tyr Val Asn Glu Ser Ser Leu Ser Thr Ser Gln
                320                 325                 330

Lys Ala Thr Tyr Ser Phe Thr Ala Thr Ala Gly Lys Pro Leu Lys Ile
            335                 340                 345

Ser Leu Val Trp Ser Asp Ala Pro Ala Ser Thr Thr Ala Ser Val Thr
        350                 355                 360

Leu Val Asn Asp Leu Asp Leu Val Ile Thr Ala Pro Asn Gly Thr Gln
    365                 370                 375

Tyr Val Gly Asn Asp Phe Thr Ser Pro Tyr Asn Asp Asn Trp Asp Gly
380                 385                 390                 395

Arg Asn Asn Val Glu Asn Val Phe Ile Asn Ala Pro Gln Ser Gly Thr
                400                 405                 410

Tyr Thr Ile Glu Val Gln Ala Tyr Asn Val Pro Val Gly Pro Gln Thr
            415                 420                 425

Phe Ser Leu Ala Ile Val Asn
        430

<210> SEQ ID NO 4
<211> LENGTH: 33
<212> TYPE: DNA
<213> ORGANISM: Artificial Sequence
<220> FEATURE:
<223> OTHER INFORMATION: primer 1

<400> SEQUENCE: 4
cggacgaata atgccagtga tccgaatggt cat                              33

<210> SEQ ID NO 5
<211> LENGTH: 33
<212> TYPE: DNA
<213> ORGANISM: Artificial Sequence
<220> FEATURE:
<223> OTHER INFORMATION: primer 2

<400> SEQUENCE: 5
aaaggaatgg cgcctcatgc gaatctagtc ttc                              33

<210> SEQ ID NO 6
<211> LENGTH: 33
<212> TYPE: DNA
<213> ORGANISM: Artificial Sequence
<220> FEATURE:

-continued

<223> OTHER INFORMATION: primer 3

<400> SEQUENCE: 6
ttcagccaag catacagtgc tggtgccaga att                33

<210> SEQ ID NO 7
<211> LENGTH: 33
<212> TYPE: DNA
<213> ORGANISM: Artificial Sequence
<220> FEATURE:
<223> OTHER INFORMATION: primer 4

<400> SEQUENCE: 7
gtcggagcta cggaaagcct ccgcccaagc ttt                33

<210> SEQ ID NO 8
<211> LENGTH: 33
<212> TYPE: DNA
<213> ORGANISM: Artificial Sequence
<220> FEATURE:
<223> OTHER INFORMATION: primer 5

<400> SEQUENCE: 8
atggcaccgg aacgtacat actatcagca aga                33

<210> SEQ ID NO 9
<211> LENGTH: 33
<212> TYPE: DNA
<213> ORGANISM: Artificial Sequence
<220> FEATURE:
<223> OTHER INFORMATION: primer 6

<400> SEQUENCE: 9
gccggtgcag ctgacgtcgg ccttggctac ccg                33

<210> SEQ ID NO 10
<211> LENGTH: 33
<212> TYPE: DNA
<213> ORGANISM: Artificial Sequence
<220> FEATURE:
<223> OTHER INFORMATION: primer 7

<400> SEQUENCE: 10
ggctacccga acggtagcca aggatgggga cga                33

<210> SEQ ID NO 11
<211> LENGTH: 1302
<212> TYPE: DNA
<213> ORGANISM: Bacillus sp. KSM-kp9860
<220> FEATURE:
<221> NAME/KEY: CDS
<222> LOCATION: (1)..(1302)
<223> OTHER INFORMATION: protease KP9860

<400> SEQUENCE: 11

```
aat gat gtg gcc aga ggt att gtg aaa gcg gat gtg gca cag agc agc      48
Asn Asp Val Ala Arg Gly Ile Val Lys Ala Asp Val Ala Gln Ser Ser
 1               5                  10                  15 tac ggt ttg tat gga caa ggc cag att gtc gca gtt gcc gat act gga      96
Tyr Gly Leu Tyr Gly Gln Gly Gln Ile Val Ala Val Ala Asp Thr Gly
             20                  25                  30 ttg gat aca gga aga aac gac agt tcg atg cat gaa gcc ttc cgc ggt     144
Leu Asp Thr Gly Arg Asn Asp Ser Ser Met His Glu Ala Phe Arg Gly
         35                  40                  45 aaa ata aca gca cta tat gca ctg ggt cgg acg aat aat gcg aat gat     192
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Lys | Ile | Thr | Ala | Leu | Tyr | Ala | Leu | Gly | Arg | Thr | Asn | Ala | Asn | Asp |     |      |
|     | 50  |     |     |     | 55  |     |     |     |     | 60  |     |     |     |     |     |      |

```
acg aac ggt cat ggt acc cat gtg gca ggt tcg gta tta gga aat ggc      240
Thr Asn Gly His Gly Thr His Val Ala Gly Ser Val Leu Gly Asn Gly
65              70                  75                  80 gca acg aat aaa gga atg gca cct caa gcg aat ctg gtt ttt caa tcc      288
Ala Thr Asn Lys Gly Met Ala Pro Gln Ala Asn Leu Val Phe Gln Ser
                85                  90                  95 atc atg gat agc agt ggt ggg ctt gga ggc ttg cct tcc aat ctg caa      336
Ile Met Asp Ser Ser Gly Gly Leu Gly Gly Leu Pro Ser Asn Leu Gln
            100                 105                 110 acc tta ttc agc caa gca ttc agt gca ggt gcc aga att cat aca aac      384
Thr Leu Phe Ser Gln Ala Phe Ser Ala Gly Ala Arg Ile His Thr Asn
        115                 120                 125 tcc tgg ggg gca gcg gtg aat ggg gcc tac acg aca gat tcc aga aat      432
Ser Trp Gly Ala Ala Val Asn Gly Ala Tyr Thr Thr Asp Ser Arg Asn
    130                 135                 140 gtg gat gac tat gta agg aaa aat gat atg acg att ctt ttc gcg gct      480
Val Asp Asp Tyr Val Arg Lys Asn Asp Met Thr Ile Leu Phe Ala Ala
145                 150                 155                 160 ggg aat gaa ggg ccg aac ggc ggt acc atc agt gca cct ggt acg gct      528
Gly Asn Glu Gly Pro Asn Gly Gly Thr Ile Ser Ala Pro Gly Thr Ala
                165                 170                 175 aaa aac gcc atc act gtc ggc gca acc gaa aac ctg cgt cca agc ttc      576
Lys Asn Ala Ile Thr Val Gly Ala Thr Glu Asn Leu Arg Pro Ser Phe
            180                 185                 190 ggt tcc tat gca gat aat att aac cac gtt gca cag ttc tct tcc cgt      624
Gly Ser Tyr Ala Asp Asn Ile Asn His Val Ala Gln Phe Ser Ser Arg
        195                 200                 205 ggc ccg aca aaa gat ggg cga atc aag cct gat gtc atg gcg cca ggg      672
Gly Pro Thr Lys Asp Gly Arg Ile Lys Pro Asp Val Met Ala Pro Gly
    210                 215                 220 aca tac att tta tca gca aga tct tct ctt gca ccc gat tcc tcc ttc      720
Thr Tyr Ile Leu Ser Ala Arg Ser Ser Leu Ala Pro Asp Ser Ser Phe
225                 230                 235                 240 tgg gcg aat cat gac agc aaa tat gcc tat atg ggt gga acg tcc atg      768
Trp Ala Asn His Asp Ser Lys Tyr Ala Tyr Met Gly Gly Thr Ser Met
                245                 250                 255 gca aca ccg att gtt gcg ggg aat gtt gca cag ctc cgt gag cat ttt      816
Ala Thr Pro Ile Val Ala Gly Asn Val Ala Gln Leu Arg Glu His Phe
            260                 265                 270 gtg aaa aat aga gga atc act cct aag cct tcc cta ttg aaa gca gct      864
Val Lys Asn Arg Gly Ile Thr Pro Lys Pro Ser Leu Leu Lys Ala Ala
        275                 280                 285 ttg att gca ggt gct gct gat gtt gga ttg ggt tat ccg aac gga aac      912
Leu Ile Ala Gly Ala Ala Asp Val Gly Leu Gly Tyr Pro Asn Gly Asn
    290                 295                 300 caa gga tgg ggc cga gtg acc ctg gat aaa tcg ttg aac gtt gcc tat      960
Gln Gly Trp Gly Arg Val Thr Leu Asp Lys Ser Leu Asn Val Ala Tyr
305                 310                 315                 320 gtg aac gaa tcc agt gcc cta tca act agc caa aaa gcg aca tat acc     1008
Val Asn Glu Ser Ser Ala Leu Ser Thr Ser Gln Lys Ala Thr Tyr Thr
                325                 330                 335 ttt act gca acg gcg ggc aag cca ttg aaa atc tcc ctg gta tgg tcg     1056
Phe Thr Ala Thr Ala Gly Lys Pro Leu Lys Ile Ser Leu Val Trp Ser
            340                 345                 350 gat gcc cct gca agc act act gct tct gta acc ctg gtc aat gat ttg     1104
Asp Ala Pro Ala Ser Thr Thr Ala Ser Val Thr Leu Val Asn Asp Leu
        355                 360                 365
```

```
gat ttg gtc att aca gca cca aac gga aca aga tat gtc ggg aat gac    1152
Asp Leu Val Ile Thr Ala Pro Asn Gly Thr Arg Tyr Val Gly Asn Asp
    370                 375                 380 ttc tca gca cca ttt gac aat aac tgg gat ggc cgc aat aac gta gaa    1200
Phe Ser Ala Pro Phe Asp Asn Asn Trp Asp Gly Arg Asn Asn Val Glu
385                 390                 395                 400 aat gta ttt att aat tcg ccc caa agt gga aca tat acc att gag gtg    1248
Asn Val Phe Ile Asn Ser Pro Gln Ser Gly Thr Tyr Thr Ile Glu Val
                405                 410                 415 caa gca tat aat gtg ccg gtt gga cca caa aac ttc tcg ttg gca att    1296
Gln Ala Tyr Asn Val Pro Val Gly Pro Gln Asn Phe Ser Leu Ala Ile
            420                 425                 430 gtg aac                                                            1302
Val Asn
```

<210> SEQ ID NO 12
<211> LENGTH: 434
<212> TYPE: PRT
<213> ORGANISM: Bacillus sp. KSM-kp9860

<400> SEQUENCE: 12

```
Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
                35                  40                  45

Lys Ile Thr Ala Leu Tyr Ala Leu Gly Arg Thr Asn Asn Ala Asn Asp
        50                  55                  60

Thr Asn Gly His Gly Thr His Val Ala Gly Ser Val Leu Gly Asn Gly
65                  70                  75                  80

Ala Thr Asn Lys Gly Met Ala Pro Gln Ala Asn Leu Val Phe Gln Ser
                85                  90                  95

Ile Met Asp Ser Ser Gly Gly Leu Gly Gly Leu Pro Ser Asn Leu Gln
            100                 105                 110

Thr Leu Phe Ser Gln Ala Phe Ser Ala Gly Ala Arg Ile His Thr Asn
        115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Tyr Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
```

```
                275                 280                 285
Leu Ile Ala Gly Ala Ala Asp Val Gly Leu Gly Tyr Pro Asn Gly Asn
    290                 295                 300
Gln Gly Trp Gly Arg Val Thr Leu Asp Lys Ser Leu Asn Val Ala Tyr
305                 310                 315                 320
Val Asn Glu Ser Ser Ala Leu Ser Thr Ser Gln Lys Ala Thr Tyr Thr
                325                 330                 335
Phe Thr Ala Thr Ala Gly Lys Pro Leu Lys Ile Ser Leu Val Trp Ser
            340                 345                 350
Asp Ala Pro Ala Ser Thr Thr Ala Ser Val Thr Leu Val Asn Asp Leu
        355                 360                 365
Asp Leu Val Ile Thr Ala Pro Asn Gly Thr Arg Tyr Val Gly Asn Asp
    370                 375                 380
Phe Ser Ala Pro Phe Asp Asn Asn Trp Asp Gly Arg Asn Asn Val Glu
385                 390                 395                 400
Asn Val Phe Ile Asn Ser Pro Gln Ser Gly Thr Tyr Thr Ile Glu Val
                405                 410                 415
Gln Ala Tyr Asn Val Pro Val Gly Pro Gln Asn Phe Ser Leu Ala Ile
            420                 425                 430
Val Asn

<210> SEQ ID NO 13
<211> LENGTH: 1302
<212> TYPE: DNA
<213> ORGANISM: Bacillus sp. KSM-9865
<220> FEATURE:
<221> NAME/KEY: CDS
<222> LOCATION: (1)..(1302)
<223> OTHER INFORMATION: Protease 9865

<400> SEQUENCE: 13 aat gat gtt gca cgt gga att gtc aaa gcg gat gtg gcg cag agc agc      48
Asn Asp Val Ala Arg Gly Ile Val Lys Ala Asp Val Ala Gln Ser Ser
1               5                   10                  15 tac ggg ttg tat gga caa gga cag atc gta gcg gtt gcc gat aca ggg      96
Tyr Gly Leu Tyr Gly Gln Gly Gln Ile Val Ala Val Ala Asp Thr Gly
            20                  25                  30 ctt gat aca ggt cgc aat gac agt tcg atg cat gaa gcc ttc cgg ggg     144
Leu Asp Thr Gly Arg Asn Asp Ser Ser Met His Glu Ala Phe Arg Gly
        35                  40                  45 aaa att act gca tta tat gca ttg gga cgg acg aat aat gcc aat gat     192
Lys Ile Thr Ala Leu Tyr Ala Leu Gly Arg Thr Asn Asn Ala Asn Asp
    50                  55                  60 acg aat ggt cat ggt acg cat gtg gct ggc tcc gta tta gga aac ggc     240
Thr Asn Gly His Gly Thr His Val Ala Gly Ser Val Leu Gly Asn Gly
65                  70                  75                  80 tcc act aat aaa gga atg gcg cct cag gcg aat cta gtc ttc caa tct     288
Ser Thr Asn Lys Gly Met Ala Pro Gln Ala Asn Leu Val Phe Gln Ser
                85                  90                  95 atc atg gat agc ggt ggg gga ctt gga gga cta cct tcg aat ctg caa     336
Ile Met Asp Ser Gly Gly Gly Leu Gly Gly Leu Pro Ser Asn Leu Gln
            100                 105                 110 acc tta ttc agc caa gca tac agt gct ggt gcc aga att cat aca aac     384
Thr Leu Phe Ser Gln Ala Tyr Ser Ala Gly Ala Arg Ile His Thr Asn
        115                 120                 125 tcc tgg gga gca gca gtg aat ggg gct tac aca aca gat tcc aga aat     432
Ser Trp Gly Ala Ala Val Asn Gly Ala Tyr Thr Thr Asp Ser Arg Asn
    130                 135                 140
```

```
gtg gat gac tat gtg cgc aaa aat gat atg acg atc ctt ttc gct gcc      480
Val Asp Asp Tyr Val Arg Lys Asn Asp Met Thr Ile Leu Phe Ala Ala
145                 150                 155                 160 ggg aat gaa gga ccg aac ggc gga acc atc agt gca cca ggc aca gct      528
Gly Asn Glu Gly Pro Asn Gly Gly Thr Ile Ser Ala Pro Gly Thr Ala
                165                 170                 175 aaa aat gca ata aca gtc gga gct acg gaa aac ctc cgc cca agc ttc      576
Lys Asn Ala Ile Thr Val Gly Ala Thr Glu Asn Leu Arg Pro Ser Phe
            180                 185                 190 ggg tct tat gcg gac aat atc aac cat gtg gca cag ttc tct tca cgt      624
Gly Ser Tyr Ala Asp Asn Ile Asn His Val Ala Gln Phe Ser Ser Arg
        195                 200                 205 gga ccg aca aag gat gga cgg atc aaa ccg gat gtc atg gca ccg gga      672
Gly Pro Thr Lys Asp Gly Arg Ile Lys Pro Asp Val Met Ala Pro Gly
    210                 215                 220 acg ttc ata cta tca gca aga tct tct ctt gca ccg gat tcc tcc ttc      720
Thr Phe Ile Leu Ser Ala Arg Ser Ser Leu Ala Pro Asp Ser Ser Phe
225                 230                 235                 240 tgg gcg aac cat gac agt aaa tat gca tac atg ggt gga acg tcc atg      768
Trp Ala Asn His Asp Ser Lys Tyr Ala Tyr Met Gly Gly Thr Ser Met
                245                 250                 255 gct aca ccg atc gtt gct gga aac gtg gca cag ctt cgt gag cat ttt      816
Ala Thr Pro Ile Val Ala Gly Asn Val Ala Gln Leu Arg Glu His Phe
                260                 265                 270 gtg aaa aac aga ggc atc aca cca aag cct tct cta tta aaa gcg gca      864
Val Lys Asn Arg Gly Ile Thr Pro Lys Pro Ser Leu Leu Lys Ala Ala
            275                 280                 285 ctg att gcc ggt gca gca gac atc ggc ctt ggc tac ccg aac ggt aac      912
Leu Ile Ala Gly Ala Ala Asp Ile Gly Leu Gly Tyr Pro Asn Gly Asn
        290                 295                 300 caa gga tgg gga cga gtg aca ttg gat aaa tcc cta aac gtt gcc tat      960
Gln Gly Trp Gly Arg Val Thr Leu Asp Lys Ser Leu Asn Val Ala Tyr
305                 310                 315                 320 gtg aac gag tcc agt tct cta tcc acc agc caa aaa gcg acg tac tcg     1008
Val Asn Glu Ser Ser Ser Leu Ser Thr Ser Gln Lys Ala Thr Tyr Ser
                325                 330                 335 ttt act gct act gcc ggc aag cct ttg aag atc tcc ctg gta tgg tct     1056
Phe Thr Ala Thr Ala Gly Lys Pro Leu Lys Ile Ser Leu Val Trp Ser
                340                 345                 350 gat gcc cct gcg agc aca act gct tcc gta acg ctt gtc aat gac ctg     1104
Asp Ala Pro Ala Ser Thr Thr Ala Ser Val Thr Leu Val Asn Asp Leu
            355                 360                 365 gac ctt gtc att acc gct cca aat ggc aca caa tat gtt gga aat gac     1152
Asp Leu Val Ile Thr Ala Pro Asn Gly Thr Gln Tyr Val Gly Asn Asp
        370                 375                 380 ttt act tcg cca tac aat aat aac tgg gat ggc cgc aat aac gta gaa     1200
Phe Thr Ser Pro Tyr Asn Asn Asn Trp Asp Gly Arg Asn Asn Val Glu
385                 390                 395                 400 aat gta ttt att aat gcg cca caa agc ggg acg tat aca att gag gta     1248
Asn Val Phe Ile Asn Ala Pro Gln Ser Gly Thr Tyr Thr Ile Glu Val
                405                 410                 415 cag gct tat aac gta ccg gtt gga cca cag acc ttc tcg ttg gca att     1296
Gln Ala Tyr Asn Val Pro Val Gly Pro Gln Thr Phe Ser Leu Ala Ile
                420                 425                 430 gtg aac                                                              1302
Val Asn

<210> SEQ ID NO 14
<211> LENGTH: 434
<212> TYPE: PRT
```

-continued

<213> ORGANISM: Bacillus sp. KSM-9865

<400> SEQUENCE: 14

| | | | | | | | | | | | | | | |
|---|---|---|---|---|---|---|---|---|---|---|---|---|---|---|
| Asn | Asp | Val | Ala | Arg | Gly | Ile | Val | Lys | Ala | Asp | Val | Ala | Gln | Ser | Ser |
| 1 | | | | 5 | | | | | 10 | | | | | 15 | |
| Tyr | Gly | Leu | Tyr | Gly | Gln | Gly | Gln | Ile | Val | Ala | Val | Ala | Asp | Thr | Gly |
| | | | 20 | | | | | 25 | | | | | 30 | | |
| Leu | Asp | Thr | Gly | Arg | Asn | Asp | Ser | Ser | Met | His | Glu | Ala | Phe | Arg | Gly |
| | | 35 | | | | | 40 | | | | | 45 | | | |
| Lys | Ile | Thr | Ala | Leu | Tyr | Ala | Leu | Gly | Arg | Thr | Asn | Asn | Ala | Asn | Asp |
| 50 | | | | | 55 | | | | | 60 | | | | | |
| Thr | Asn | Gly | His | Gly | Thr | His | Val | Ala | Gly | Ser | Val | Leu | Gly | Asn | Gly |
| 65 | | | | 70 | | | | | 75 | | | | | 80 | |
| Ser | Thr | Asn | Lys | Gly | Met | Ala | Pro | Gln | Ala | Asn | Leu | Val | Phe | Gln | Ser |
| | | | | 85 | | | | | 90 | | | | | 95 | |
| Ile | Met | Asp | Ser | Gly | Gly | Gly | Leu | Gly | Gly | Leu | Pro | Ser | Asn | Leu | Gln |
| | | | 100 | | | | | 105 | | | | | 110 | | |
| Thr | Leu | Phe | Ser | Gln | Ala | Tyr | Ser | Ala | Gly | Ala | Arg | Ile | His | Thr | Asn |
| | | 115 | | | | | 120 | | | | | 125 | | | |
| Ser | Trp | Gly | Ala | Ala | Val | Asn | Gly | Ala | Tyr | Thr | Thr | Asp | Ser | Arg | Asn |
| | 130 | | | | | 135 | | | | | 140 | | | | |
| Val | Asp | Asp | Tyr | Val | Arg | Lys | Asn | Asp | Met | Thr | Ile | Leu | Phe | Ala | Ala |
| 145 | | | | | 150 | | | | | 155 | | | | | 160 |
| Gly | Asn | Glu | Gly | Pro | Asn | Gly | Gly | Thr | Ile | Ser | Ala | Pro | Gly | Thr | Ala |
| | | | | 165 | | | | | 170 | | | | | 175 | |
| Lys | Asn | Ala | Ile | Thr | Val | Gly | Ala | Thr | Glu | Asn | Leu | Arg | Pro | Ser | Phe |
| | | | 180 | | | | | 185 | | | | | 190 | | |
| Gly | Ser | Tyr | Ala | Asp | Asn | Ile | Asn | His | Val | Ala | Gln | Phe | Ser | Ser | Arg |
| | | 195 | | | | | 200 | | | | | 205 | | | |
| Gly | Pro | Thr | Lys | Asp | Gly | Arg | Ile | Lys | Pro | Asp | Val | Met | Ala | Pro | Gly |
| | 210 | | | | | 215 | | | | | 220 | | | | |
| Thr | Phe | Ile | Leu | Ser | Ala | Arg | Ser | Ser | Leu | Ala | Pro | Asp | Ser | Ser | Phe |
| 225 | | | | | 230 | | | | | 235 | | | | | 240 |
| Trp | Ala | Asn | His | Asp | Ser | Lys | Tyr | Ala | Tyr | Met | Gly | Gly | Thr | Ser | Met |
| | | | | 245 | | | | | 250 | | | | | 255 | |
| Ala | Thr | Pro | Ile | Val | Ala | Gly | Asn | Val | Ala | Gln | Leu | Arg | Glu | His | Phe |
| | | | 260 | | | | | 265 | | | | | 270 | | |
| Val | Lys | Asn | Arg | Gly | Ile | Thr | Pro | Lys | Pro | Ser | Leu | Leu | Lys | Ala | Ala |
| | | 275 | | | | | 280 | | | | | 285 | | | |
| Leu | Ile | Ala | Gly | Ala | Ala | Asp | Ile | Gly | Leu | Gly | Tyr | Pro | Asn | Gly | Asn |
| | 290 | | | | | 295 | | | | | 300 | | | | |
| Gln | Gly | Trp | Gly | Arg | Val | Thr | Leu | Asp | Lys | Ser | Leu | Asn | Val | Ala | Tyr |
| 305 | | | | | 310 | | | | | 315 | | | | | 320 |
| Val | Asn | Glu | Ser | Ser | Ser | Leu | Ser | Thr | Ser | Gln | Lys | Ala | Thr | Tyr | Ser |
| | | | | 325 | | | | | 330 | | | | | 335 | |
| Phe | Thr | Ala | Thr | Ala | Gly | Lys | Pro | Leu | Lys | Ile | Ser | Leu | Val | Trp | Ser |
| | | | 340 | | | | | 345 | | | | | 350 | | |
| Asp | Ala | Pro | Ala | Ser | Thr | Thr | Ala | Ser | Val | Thr | Leu | Val | Asn | Asp | Leu |
| | | 355 | | | | | 360 | | | | | 365 | | | |
| Asp | Leu | Val | Ile | Thr | Ala | Pro | Asn | Gly | Thr | Gln | Tyr | Val | Gly | Asn | Asp |
| | 370 | | | | | 375 | | | | | 380 | | | | |
| Phe | Thr | Ser | Pro | Tyr | Asn | Asn | Asn | Trp | Asp | Gly | Arg | Asn | Asn | Val | Glu |
| 385 | | | | | 390 | | | | | 395 | | | | | 400 |

```
Asn Val Phe Ile Asn Ala Pro Gln Ser Gly Thr Tyr Thr Ile Glu Val
            405                 410                 415

Gln Ala Tyr Asn Val Pro Val Gly Pro Gln Thr Phe Ser Leu Ala Ile
            420                 425                 430

Val Asn

<210> SEQ ID NO 15
<211> LENGTH: 1299
<212> TYPE: DNA
<213> ORGANISM: Bacillus sp. D-6
<220> FEATURE:
<221> NAME/KEY: CDS
<222> LOCATION: (1)..(1299)
<223> OTHER INFORMATION: Protease E-1

<400> SEQUENCE: 15 aat gat gta gca aga gga ata gta aaa gca gac gtt gca caa aac aat     48
Asn Asp Val Ala Arg Gly Ile Val Lys Ala Asp Val Ala Gln Asn Asn
1               5                   10                  15 tac gga cta tat gga caa ggt caa gta gtt gca gta gcg gat acg ggt     96
Tyr Gly Leu Tyr Gly Gln Gly Gln Val Val Ala Val Ala Asp Thr Gly
            20                  25                  30 tta gat aca ggt cgt aac gat agt tct atg cat gaa gca ttc cgt ggg    144
Leu Asp Thr Gly Arg Asn Asp Ser Ser Met His Glu Ala Phe Arg Gly
        35                  40                  45 aaa att aca gct ctt tac gcg tta gga aga act aac aat gca aat gat    192
Lys Ile Thr Ala Leu Tyr Ala Leu Gly Arg Thr Asn Asn Ala Asn Asp
    50                  55                  60 ccg aat ggg cat ggt acg cat gta gct ggt tct gtg ctt ggt aat gct    240
Pro Asn Gly His Gly Thr His Val Ala Gly Ser Val Leu Gly Asn Ala
65                  70                  75                  80 tta aat aaa gga atg gct ccg caa gct aac tta gtc ttc caa tct att    288
Leu Asn Lys Gly Met Ala Pro Gln Ala Asn Leu Val Phe Gln Ser Ile
                85                  90                  95 atg gat agc agc gga gga tta gga gga tta cca tcg aat tta aat acg    336
Met Asp Ser Ser Gly Gly Leu Gly Gly Leu Pro Ser Asn Leu Asn Thr
            100                 105                 110 tta ttt agt caa gct tgg aat gct ggc gct aga att cat act aac tct    384
Leu Phe Ser Gln Ala Trp Asn Ala Gly Ala Arg Ile His Thr Asn Ser
        115                 120                 125 tgg ggg gcc cca gta aat gga gcg tac act gct aac tcg aga caa gtg    432
Trp Gly Ala Pro Val Asn Gly Ala Tyr Thr Ala Asn Ser Arg Gln Val
    130                 135                 140 gat gag tat gtt cga aac aat gat atg acg gta ctt ttt gca gct gga    480
Asp Glu Tyr Val Arg Asn Asn Asp Met Thr Val Leu Phe Ala Ala Gly
145                 150                 155                 160 aat gaa gga cct aac tct gga aca att agc gct cca ggg aca gcg aaa    528
Asn Glu Gly Pro Asn Ser Gly Thr Ile Ser Ala Pro Gly Thr Ala Lys
                165                 170                 175 aat gcc att acg gtc ggc gca acg gaa aac tac cga cca agt ttt ggt    576
Asn Ala Ile Thr Val Gly Ala Thr Glu Asn Tyr Arg Pro Ser Phe Gly
            180                 185                 190 tca att gca gat aac cct aat cat atc gca caa ttt tca tcg aga gga    624
Ser Ile Ala Asp Asn Pro Asn His Ile Ala Gln Phe Ser Ser Arg Gly
        195                 200                 205 gct acg aga gat gga cga att aaa cca gac gta aca gct cct gga aca    672
Ala Thr Arg Asp Gly Arg Ile Lys Pro Asp Val Thr Ala Pro Gly Thr
    210                 215                 220 ttt ata tta tca gca cgc tct tct tta gca cca gac tct tcg ttt tgg    720
Phe Ile Leu Ser Ala Arg Ser Ser Leu Ala Pro Asp Ser Ser Phe Trp
225                 230                 235                 240
```

```
gcg aat tat aac agt aag tat gcg tat atg ggc ggt acc tct atg gcg        768
Ala Asn Tyr Asn Ser Lys Tyr Ala Tyr Met Gly Gly Thr Ser Met Ala
            245                 250                 255 aca cct ata gtt gcg ggg aat gtc gcg caa tta cgc gag cat ttt ata        816
Thr Pro Ile Val Ala Gly Asn Val Ala Gln Leu Arg Glu His Phe Ile
        260                 265                 270 aaa aat aga gga att aca cct aaa cct tcc tta ata aaa gct gca ctt        864
Lys Asn Arg Gly Ile Thr Pro Lys Pro Ser Leu Ile Lys Ala Ala Leu
    275                 280                 285 atc gct ggg gct act gat gtt ggt tta gga tat cca agt ggt gac caa        912
Ile Ala Gly Ala Thr Asp Val Gly Leu Gly Tyr Pro Ser Gly Asp Gln
290                 295                 300 ggc tgg ggg cgt gtt act tta gat aaa tcg tta aat gta gcg tat gtc        960
Gly Trp Gly Arg Val Thr Leu Asp Lys Ser Leu Asn Val Ala Tyr Val
305                 310                 315                 320 aat gaa gca act gca tta aca aca gga caa aaa gca acg tat tcg ttc       1008
Asn Glu Ala Thr Ala Leu Thr Thr Gly Gln Lys Ala Thr Tyr Ser Phe
                325                 330                 335 caa acg caa gcg ggt aaa cca tta aaa atc tcg tta gta tgg aca gat       1056
Gln Thr Gln Ala Gly Lys Pro Leu Lys Ile Ser Leu Val Trp Thr Asp
            340                 345                 350 gca cct gga agt aca aca gca tct tat aca cta gtt aat gat tta gat       1104
Ala Pro Gly Ser Thr Thr Ala Ser Tyr Thr Leu Val Asn Asp Leu Asp
        355                 360                 365 cta gtt att act gct ccg aat gga caa aaa tat gta ggt aat gat ttt       1152
Leu Val Ile Thr Ala Pro Asn Gly Gln Lys Tyr Val Gly Asn Asp Phe
    370                 375                 380 agt tat cct tat gat aat aat tgg gat ggt cgc aac aat gtt gag aac       1200
Ser Tyr Pro Tyr Asp Asn Asn Trp Asp Gly Arg Asn Asn Val Glu Asn
385                 390                 395                 400 gta ttt ata aac gct ccg caa tct gga acg tat aca att gag gtt caa       1248
Val Phe Ile Asn Ala Pro Gln Ser Gly Thr Tyr Thr Ile Glu Val Gln
                405                 410                 415 gcg tat aac gtt cca tct gga cca cag cgt ttc tca cta gct atc gta       1296
Ala Tyr Asn Val Pro Ser Gly Pro Gln Arg Phe Ser Leu Ala Ile Val
            420                 425                 430 cat                                                                    1299
His

<210> SEQ ID NO 16
<211> LENGTH: 433
<212> TYPE: PRT
<213> ORGANISM: Bacillus sp. D-6

<400> SEQUENCE: 16

Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Gly Leu Gly Gly Leu Pro Ser Asn Leu Asn Thr
```

100                 105                 110
Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Ile Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
    210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Ser Gly Asp Gln
    290                 295                 300

Gly Trp Gly Arg Val Thr Leu Asp Lys Ser Leu Asn Val Ala Tyr Val
305                 310                 315                 320

Asn Glu Ala Thr Ala Leu Thr Thr Gly Gln Lys Ala Thr Tyr Ser Phe
                325                 330                 335

Gln Thr Gln Ala Gly Lys Pro Leu Lys Ile Ser Leu Val Trp Thr Asp
            340                 345                 350

Ala Pro Gly Ser Thr Thr Ala Ser Tyr Thr Leu Val Asn Asp Leu Asp
        355                 360                 365

Leu Val Ile Thr Ala Pro Asn Gly Gln Lys Tyr Val Gly Asn Asp Phe
    370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Ile Glu Val Gln
                405                 410                 415

Ala Tyr Asn Val Pro Ser Gly Pro Gln Arg Phe Ser Leu Ala Ile Val
            420                 425                 430

His

<210> SEQ ID NO 17
<211> LENGTH: 1299
<212> TYPE: DNA
<213> ORGANISM: Bacillus sp. Y
<220> FEATURE:
<221> NAME/KEY: CDS
<222> LOCATION: (1)..(1299)
<223> OTHER INFORMATION: Gene name Ya,
      Protease Ya

<400> SEQUENCE: 17 aat gat gta gca aga ggg ata gta aaa gct gat gtt gca caa aac aat       48
Asn Asp Val Ala Arg Gly Ile Val Lys Ala Asp Val Ala Gln Asn Asn

```
tac gga tta tat gga caa ggt caa gta gtt gca gta gcg gac aca ggc      96
Tyr Gly Leu Tyr Gly Gln Gly Gln Val Val Ala Val Ala Asp Thr Gly
            20                  25                  30 tta gat aca ggt cgt aac gat agt tct atg cat gaa gca ttc cgc ggg     144
Leu Asp Thr Gly Arg Asn Asp Ser Ser Met His Glu Ala Phe Arg Gly
        35                  40                  45 aaa atc aca gct ctt tac gcg tta gga aga act aat aat gcg agt gat     192
Lys Ile Thr Ala Leu Tyr Ala Leu Gly Arg Thr Asn Asn Ala Ser Asp
    50                  55                  60 ccg aat ggg cat ggc aca cat gta gca ggt tct gta ctt ggt aat gct     240
Pro Asn Gly His Gly Thr His Val Ala Gly Ser Val Leu Gly Asn Ala
65                  70                  75                  80 tta aat aaa gga atg gct ccg caa gct aac tta gtc ttc caa tct att     288
Leu Asn Lys Gly Met Ala Pro Gln Ala Asn Leu Val Phe Gln Ser Ile
                85                  90                  95 atg gat agc agc gga gga tta ggt ggc tta cca tcg aac tta aat acg     336
Met Asp Ser Ser Gly Gly Leu Gly Gly Leu Pro Ser Asn Leu Asn Thr
            100                 105                 110 tta ttt agt caa gct tgg aat gct gga gca aga att cat act aac tct     384
Leu Phe Ser Gln Ala Trp Asn Ala Gly Ala Arg Ile His Thr Asn Ser
        115                 120                 125 tgg gga gcc cca gta aat gga gcg tac act gct aac tcg aga caa gtg     432
Trp Gly Ala Pro Val Asn Gly Ala Tyr Thr Ala Asn Ser Arg Gln Val
    130                 135                 140 gat gaa tat gtt cga aat aat gat atg acg gta ctt ttt gca gct ggt     480
Asp Glu Tyr Val Arg Asn Asn Asp Met Thr Val Leu Phe Ala Ala Gly
145                 150                 155                 160 aat gaa ggt cct aat tca gga aca att agt gct cca ggt aca gcg aaa     528
Asn Glu Gly Pro Asn Ser Gly Thr Ile Ser Ala Pro Gly Thr Ala Lys
                165                 170                 175 aat gct att acg gtc ggc gca acg gaa aac tat cgc cca agc ttc ggt     576
Asn Ala Ile Thr Val Gly Ala Thr Glu Asn Tyr Arg Pro Ser Phe Gly
            180                 185                 190 tcg ata gca gat aac cca aat cat att gca caa ttt tca tcg aga gga     624
Ser Ile Ala Asp Asn Pro Asn His Ile Ala Gln Phe Ser Ser Arg Gly
        195                 200                 205 gct acg agg gat gga cga att aag cct gac gta aca gct cct gga aca     672
Ala Thr Arg Asp Gly Arg Ile Lys Pro Asp Val Thr Ala Pro Gly Thr
    210                 215                 220 ttt att tta tca gca cgt tct tcc tta gct cca gac tct tcg ttt tgg     720
Phe Ile Leu Ser Ala Arg Ser Ser Leu Ala Pro Asp Ser Ser Phe Trp
225                 230                 235                 240 gcg aat tat aac agt aaa tac gcg tat atg ggc ggt acc tcc atg gcg     768
Ala Asn Tyr Asn Ser Lys Tyr Ala Tyr Met Gly Gly Thr Ser Met Ala
                245                 250                 255 aca cct att gtt gca ggg aat gtc gcg caa tta cgt gag cat ttt ata     816
Thr Pro Ile Val Ala Gly Asn Val Ala Gln Leu Arg Glu His Phe Ile
            260                 265                 270 aaa aat aga ggt att act cct aag cct tct tta ata aaa gct gca ctt     864
Lys Asn Arg Gly Ile Thr Pro Lys Pro Ser Leu Ile Lys Ala Ala Leu
        275                 280                 285 atc gct ggt gct act gat gtt ggt tta gga tat cct aat ggt gac caa     912
Ile Ala Gly Ala Thr Asp Val Gly Leu Gly Tyr Pro Asn Gly Asp Gln
    290                 295                 300 ggc tgg ggg cgt gtt act cta aat aaa tcg tta aat gta gcg tat gtc     960
Gly Trp Gly Arg Val Thr Leu Asn Lys Ser Leu Asn Val Ala Tyr Val
305                 310                 315                 320 aat gaa gca act gca tta gcc aca gga caa aaa gca acg tat tcg ttc    1008
```

```
                Asn Glu Ala Thr Ala Leu Ala Thr Gly Gln Lys Ala Thr Tyr Ser Phe
                                325                 330                 335 caa gca caa gcg ggt aaa cct tta aaa atc tcg tta gta tgg aca gat                    1056
Gln Ala Gln Ala Gly Lys Pro Leu Lys Ile Ser Leu Val Trp Thr Asp
            340                 345                 350 gct cct gga agt aca act gca tct tat aca cta gtt aat gat tta gat                    1104
Ala Pro Gly Ser Thr Thr Ala Ser Tyr Thr Leu Val Asn Asp Leu Asp
        355                 360                 365 cta gtt att act gct ccg aat gga caa aaa tat gta gga aat gat ttt                    1152
Leu Val Ile Thr Ala Pro Asn Gly Gln Lys Tyr Val Gly Asn Asp Phe
    370                 375                 380 agt tat cct tat gat aat aac tgg gat ggt cgc aac aat gtt gag aac                    1200
Ser Tyr Pro Tyr Asp Asn Asn Trp Asp Gly Arg Asn Asn Val Glu Asn
385                 390                 395                 400 gta ttt ata aac gct ccg caa tct gga acg tat ata att gag gtt caa                    1248
Val Phe Ile Asn Ala Pro Gln Ser Gly Thr Tyr Ile Ile Glu Val Gln
                405                 410                 415 gcg tat aat gta cca tct ggc cca cag cgt ttc tca cta gct atc gta                    1296
Ala Tyr Asn Val Pro Ser Gly Pro Gln Arg Phe Ser Leu Ala Ile Val
            420                 425                 430 cat                                                                                1299
His <210> SEQ ID NO 18
<211> LENGTH: 433
<212> TYPE: PRT
<213> ORGANISM: Bacillus sp. Y

<400> SEQUENCE: 18

Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Ser Asp
    50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Gly Leu Gly Leu Pro Ser Asn Leu Asn Thr
            100                 105                 110

Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
    130                 135                 140

Asp Glu Tyr Val Arg Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Ile Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
    210                 215                 220
```

-continued

```
Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
            245                 250                 255

Thr Pro Ile Val Ala Gly Asn Val Ala Gln Leu Arg Glu His Phe Ile
        260                 265                 270

Lys Asn Arg Gly Ile Thr Pro Lys Pro Ser Leu Ile Lys Ala Ala Leu
    275                 280                 285

Ile Ala Gly Ala Thr Asp Val Gly Leu Gly Tyr Pro Asn Gly Asp Gln
290                 295                 300

Gly Trp Gly Arg Val Thr Leu Asn Lys Ser Leu Asn Val Ala Tyr Val
305                 310                 315                 320

Asn Glu Ala Thr Ala Leu Ala Thr Gly Gln Lys Ala Thr Tyr Ser Phe
            325                 330                 335

Gln Ala Gln Ala Gly Lys Pro Leu Lys Ile Ser Leu Val Trp Thr Asp
        340                 345                 350

Ala Pro Gly Ser Thr Thr Ala Ser Tyr Thr Leu Val Asn Asp Leu Asp
    355                 360                 365

Leu Val Ile Thr Ala Pro Asn Gly Gln Lys Tyr Val Gly Asn Asp Phe
370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Ile Ile Glu Val Gln
            405                 410                 415

Ala Tyr Asn Val Pro Ser Gly Pro Gln Arg Phe Ser Leu Ala Ile Val
        420                 425                 430

His
```

```
<210> SEQ ID NO 19
<211> LENGTH: 1299
<212> TYPE: DNA
<213> ORGANISM: Bacillus SD521
<220> FEATURE:
<221> NAME/KEY: CDS
<222> LOCATION: (1)..(1299)
<223> OTHER INFORMATION: Gene name SD-521, protease SD521

<400> SEQUENCE: 19 aat gat gta gca aga gga ata gta aaa gca gac gtt gca caa aac aat     48
Asn Asp Val Ala Arg Gly Ile Val Lys Ala Asp Val Ala Gln Asn Asn
1               5                   10                  15 tac gga cta tat gga caa ggt caa gta gtt gca gta gcg gat acg ggt     96
Tyr Gly Leu Tyr Gly Gln Gly Gln Val Val Ala Val Ala Asp Thr Gly
            20                  25                  30 tta gat aca ggt cgt aac gat agt tct atg cat gaa gca ttc cgt ggg    144
Leu Asp Thr Gly Arg Asn Asp Ser Ser Met His Glu Ala Phe Arg Gly
        35                  40                  45 aaa att aca gct ctt tac gcg tta gga aga act aac aat gca aat gat    192
Lys Ile Thr Ala Leu Tyr Ala Leu Gly Arg Thr Asn Asn Ala Asn Asp
    50                  55                  60 ccg aat ggg cat ggt acg cat gta gca ggt tct gta ctt ggt aat gct    240
Pro Asn Gly His Gly Thr His Val Ala Gly Ser Val Leu Gly Asn Ala
65                  70                  75                  80 tta aat aaa gga atg gct ccg caa gct aac tta gtc ttc caa tct att    288
Leu Asn Lys Gly Met Ala Pro Gln Ala Asn Leu Val Phe Gln Ser Ile
                85                  90                  95 atg gat agc agc gga gga tta ggt gga tta cca tcg aat ttg aat acg    336
```

```
                Met Asp Ser Ser Gly Gly Leu Gly Gly Leu Pro Ser Asn Leu Asn Thr
                            100                 105                 110 tta ttt agt caa gct tgg aat gct ggg gct aga att cat act aac tct          384
Leu Phe Ser Gln Ala Trp Asn Ala Gly Ala Arg Ile His Thr Asn Ser
            115                 120                 125 tgg ggt gct cca gta aat gga gcg tac act gct aac tcg aga caa gtg          432
Trp Gly Ala Pro Val Asn Gly Ala Tyr Thr Ala Asn Ser Arg Gln Val
130                 135                 140 gat gag tat gtt cga aat aat gat atg acg gta ctt ttt gca gca ggt          480
Asp Glu Tyr Val Arg Asn Asn Asp Met Thr Val Leu Phe Ala Ala Gly
145                 150                 155                 160 aat gaa ggt cct aat tca gga aca att agt gct cca ggc aca gcg aaa          528
Asn Glu Gly Pro Asn Ser Gly Thr Ile Ser Ala Pro Gly Thr Ala Lys
                165                 170                 175 aat gcc att acg gtc ggc gca acg gaa aac tat cgc ccg agc ttc ggt          576
Asn Ala Ile Thr Val Gly Ala Thr Glu Asn Tyr Arg Pro Ser Phe Gly
            180                 185                 190 tca tta gca gat aac cca aat cat atc gca caa ttt tca tca aga gga          624
Ser Leu Ala Asp Asn Pro Asn His Ile Ala Gln Phe Ser Ser Arg Gly
        195                 200                 205 gct acg aga gat gga cga att aaa cca gac gta aca gct cct gga aca          672
Ala Thr Arg Asp Gly Arg Ile Lys Pro Asp Val Thr Ala Pro Gly Thr
210                 215                 220 ttt att tta tca gca cgt tct tcc tta gcc cca gac tct tcg ttt tgg          720
Phe Ile Leu Ser Ala Arg Ser Ser Leu Ala Pro Asp Ser Ser Phe Trp
225                 230                 235                 240 gcg aat tat aac agt aag tat gcg tac atg ggc ggt acc tct atg gcg          768
Ala Asn Tyr Asn Ser Lys Tyr Ala Tyr Met Gly Gly Thr Ser Met Ala
                245                 250                 255 aca cct ata gtt gcg ggg aat gtc gcg caa tta cgc gag cat ttt ata          816
Thr Pro Ile Val Ala Gly Asn Val Ala Gln Leu Arg Glu His Phe Ile
            260                 265                 270 aaa aat aga gga att aca cct aaa cct tcc tta ata aaa gct gca ctt          864
Lys Asn Arg Gly Ile Thr Pro Lys Pro Ser Leu Ile Lys Ala Ala Leu
        275                 280                 285 atc gct ggg gct act gat gtt ggt tta gga tat cca agt ggt gac caa          912
Ile Ala Gly Ala Thr Asp Val Gly Leu Gly Tyr Pro Ser Gly Asp Gln
290                 295                 300 ggc tgg ggg cgt gtt act cta gat aaa tcg tta aat gta gcg tat gtc          960
Gly Trp Gly Arg Val Thr Leu Asp Lys Ser Leu Asn Val Ala Tyr Val
305                 310                 315                 320 aat gaa gca act gca tta gca aca gga caa aaa gca acg tat tcg ttc         1008
Asn Glu Ala Thr Ala Leu Ala Thr Gly Gln Lys Ala Thr Tyr Ser Phe
                325                 330                 335 caa gca caa gcg ggt aaa cct tta aaa atc tcg tta gta tgg aca gat         1056
Gln Ala Gln Ala Gly Lys Pro Leu Lys Ile Ser Leu Val Trp Thr Asp
            340                 345                 350 gca cct gga agt aca act gca tct tat aca cta gtt aat gat tta gat         1104
Ala Pro Gly Ser Thr Thr Ala Ser Tyr Thr Leu Val Asn Asp Leu Asp
        355                 360                 365 cta gtt att act gct ccg aat gga caa aaa tat gta gga aat gat ttt         1152
Leu Val Ile Thr Ala Pro Asn Gly Gln Lys Tyr Val Gly Asn Asp Phe
370                 375                 380 agt tat cct tat gat aat aac tgg gat ggt cgc aac aat gtt gag aac         1200
Ser Tyr Pro Tyr Asp Asn Asn Trp Asp Gly Arg Asn Asn Val Glu Asn
385                 390                 395                 400 gta ttt ata aac gct ccg caa tct gga acg tat aca att gag gtt caa         1248
Val Phe Ile Asn Ala Pro Gln Ser Gly Thr Tyr Thr Ile Glu Val Gln
                405                 410                 415
```

```
gcg tat aat gta cca tct ggc cca cag cgt ttc tca cta gct atc gta    1296
Ala Tyr Asn Val Pro Ser Gly Pro Gln Arg Phe Ser Leu Ala Ile Val
        420                 425                 430 cat                                                                 1299
His
```

<210> SEQ ID NO 20
<211> LENGTH: 433
<212> TYPE: PRT
<213> ORGANISM: Bacillus SD521

<400> SEQUENCE: 20

```
Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Leu Gly Gly Leu Pro Ser Asn Leu Asn Thr
                100                 105                 110

Leu Phe Ser Gln Ala Trp Asn Ala Gly Ala Arg Ile His Thr Asn Ser
            115                 120                 125

Trp Gly Ala Pro Val Asn Gly Ala Tyr Thr Ala Asn Ser Arg Gln Val
        130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Leu Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
    210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Ser Gly Asp Gln
    290                 295                 300

Gly Trp Gly Arg Val Thr Leu Asp Lys Ser Leu Asn Val Ala Tyr Val
305                 310                 315                 320

Asn Glu Ala Thr Ala Leu Ala Thr Gly Gln Lys Ala Thr Tyr Ser Phe
                325                 330                 335

Gln Ala Gln Ala Gly Lys Pro Leu Lys Ile Ser Leu Val Trp Thr Asp
```

```
                340                 345                 350
Ala Pro Gly Ser Thr Thr Ala Ser Tyr Thr Leu Val Asn Asp Leu Asp
            355                 360                 365

Leu Val Ile Thr Ala Pro Asn Gly Gln Lys Tyr Val Gly Asn Asp Phe
        370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Ile Glu Val Gln
                405                 410                 415

Ala Tyr Asn Val Pro Ser Gly Pro Gln Arg Phe Ser Leu Ala Ile Val
                420                 425                 430

His

<210> SEQ ID NO 21
<211> LENGTH: 1302
<212> TYPE: DNA
<213> ORGANISM: Bacillus NCIB12289
<220> FEATURE:
<221> NAME/KEY: CDS
<222> LOCATION: (1)..(1302)
<223> OTHER INFORMATION: Gene name A1, protease A1

<400> SEQUENCE: 21 aac gat gtt gcc aga ggc att gta aaa gcc gat gtt gcc cag agc agc      48
Asn Asp Val Ala Arg Gly Ile Val Lys Ala Asp Val Ala Gln Ser Ser
1               5                   10                  15 tat ggt tta tat ggg caa ggg caa gtg gtt gca gta gcg gat acc gga      96
Tyr Gly Leu Tyr Gly Gln Gly Gln Val Val Ala Val Ala Asp Thr Gly
            20                  25                  30 ctg gat aca ggg cgt aat gac agc tcg atg cat gaa gcg ttc cga gga     144
Leu Asp Thr Gly Arg Asn Asp Ser Ser Met His Glu Ala Phe Arg Gly
        35                  40                  45 aag att acc gcg ata tat gcc ctt gga aga aca aac aac gcc aat gat     192
Lys Ile Thr Ala Ile Tyr Ala Leu Gly Arg Thr Asn Asn Ala Asn Asp
    50                  55                  60 cca aac gga cac ggg acg cat gtt gcc gga tct gtt tta gga aac ggt     240
Pro Asn Gly His Gly Thr His Val Ala Gly Ser Val Leu Gly Asn Gly
65                  70                  75                  80 act tcg aat aaa ggg atg gct cca caa gct aac tta gtt ttc caa tct     288
Thr Ser Asn Lys Gly Met Ala Pro Gln Ala Asn Leu Val Phe Gln Ser
                85                  90                  95 gtt atg gac agc aat ggc gga ctt ggc gga ctg cct tcc aat gta agt     336
Val Met Asp Ser Asn Gly Gly Leu Gly Gly Leu Pro Ser Asn Val Ser
            100                 105                 110 aca tta ttc agc cag gca tat agt gcc ggt gcc aga atc cat acg aac     384
Thr Leu Phe Ser Gln Ala Tyr Ser Ala Gly Ala Arg Ile His Thr Asn
        115                 120                 125 tca tgg gga gcg cct gta aac gga gcg tac act act gat tcc aga aac     432
Ser Trp Gly Ala Pro Val Asn Gly Ala Tyr Thr Thr Asp Ser Arg Asn
    130                 135                 140 gta gac gat tat gtt cgt aaa aat gat atg gcg gtt ctt ttt gca gcg     480
Val Asp Asp Tyr Val Arg Lys Asn Asp Met Ala Val Leu Phe Ala Ala
145                 150                 155                 160 ggt aac gaa ggg ccg aat ggc ggc aca atc agt gct cct ggt acc gcg     528
Gly Asn Glu Gly Pro Asn Gly Gly Thr Ile Ser Ala Pro Gly Thr Ala
                165                 170                 175 aag aat gct atc aca gta ggg gca aca gaa aac ctg cgc cca agc ttt     576
Lys Asn Ala Ile Thr Val Gly Ala Thr Glu Asn Leu Arg Pro Ser Phe
            180                 185                 190
```

-continued

| | | |
|---|---|---|
| gga tct tat gct gac aac atc aat cat gta gca cag ttt tcc tcc cgc<br>Gly Ser Tyr Ala Asp Asn Ile Asn His Val Ala Gln Phe Ser Ser Arg<br>     195                            200                        205 | | 624 |
| gga cct aca aag gat gga cgt atc aaa ccg gac gta atg gca cca gga<br>Gly Pro Thr Lys Asp Gly Arg Ile Lys Pro Asp Val Met Ala Pro Gly<br>210                         215                            220 | | 672 |
| aca ttt att tta tcg gca aga tct tct ttg gct ccg gac tcc tca ttc<br>Thr Phe Ile Leu Ser Ala Arg Ser Ser Leu Ala Pro Asp Ser Ser Phe<br>225                         230                        235                    240 | | 720 |
| tgg gca aac cat gac agc aaa tat gct tat atg ggt gga aca tcc atg<br>Trp Ala Asn His Asp Ser Lys Tyr Ala Tyr Met Gly Gly Thr Ser Met<br>                         245                        250                        255 | | 768 |
| gcg aca ccg att gta gct ggt aac gtt gca cag tta cgt gaa cat ttc<br>Ala Thr Pro Ile Val Ala Gly Asn Val Ala Gln Leu Arg Glu His Phe<br>                         260                        265                        270 | | 816 |
| atc aaa aac aga gga atc act cct aaa cca tcc ttg ctg aaa gca gct<br>Ile Lys Asn Arg Gly Ile Thr Pro Lys Pro Ser Leu Leu Lys Ala Ala<br>                         275                        280                        285 | | 864 |
| ctt att gcc gga gca act gat atc ggt ctt ggc tat ccg agt gga aac<br>Leu Ile Ala Gly Ala Thr Asp Ile Gly Leu Gly Tyr Pro Ser Gly Asn<br>          290                        295                        300 | | 912 |
| caa gga tgg gga aga gta aca ttg gac aag tca ctt aat gta gct ttc<br>Gln Gly Trp Gly Arg Val Thr Leu Asp Lys Ser Leu Asn Val Ala Phe<br>305                         310                        315                    320 | | 960 |
| gta aat gaa aca agc tct tta tct act aac caa aag gct acg tat tca<br>Val Asn Glu Thr Ser Ser Leu Ser Thr Asn Gln Lys Ala Thr Tyr Ser<br>                         325                        330                        335 | | 1008 |
| ttt act gca caa tca ggc aaa cct ttg aag att tca ttg gtt tgg tct<br>Phe Thr Ala Gln Ser Gly Lys Pro Leu Lys Ile Ser Leu Val Trp Ser<br>                         340                        345                    350 | | 1056 |
| gat gca ccg gca agt act tcc gca tcg gtt aca ttg gtg aat gat ctg<br>Asp Ala Pro Ala Ser Thr Ser Ala Ser Val Thr Leu Val Asn Asp Leu<br>          355                        360                        365 | | 1104 |
| gat ctg gtg att aca gct cca aat gga aca aag tat gtt gga aac gac<br>Asp Leu Val Ile Thr Ala Pro Asn Gly Thr Lys Tyr Val Gly Asn Asp<br>370                         375                        380 | | 1152 |
| ttt act gct ccc tat gat aat aac tgg gat gga cgt aac aat gta gag<br>Phe Thr Ala Pro Tyr Asp Asn Asn Trp Asp Gly Arg Asn Asn Val Glu<br>385                         390                        395                    400 | | 1200 |
| aac gtg ttt atc aat gct ccg caa agc gga acg tat aca gtt gag gta<br>Asn Val Phe Ile Asn Ala Pro Gln Ser Gly Thr Tyr Thr Val Glu Val<br>                         405                        410                        415 | | 1248 |
| cag gct tac aat gtt cca caa ggg ccg cag gcg ttt tct ttg gct att<br>Gln Ala Tyr Asn Val Pro Gln Gly Pro Gln Ala Phe Ser Leu Ala Ile<br>                         420                        425                    430 | | 1296 |
| gtg aac<br>Val Asn | | 1302 |

<210> SEQ ID NO 22
<211> LENGTH: 434
<212> TYPE: PRT
<213> ORGANISM: Bacillus NCIB12289

<400> SEQUENCE: 22

Asn Asp Val Ala Arg Gly Ile Val Lys Ala Asp Val Ala Gln Ser Ser
1                   5                   10                   15

Tyr Gly Leu Tyr Gly Gln Gly Gln Val Val Ala Val Ala Asp Thr Gly
                 20                   25                   30

Leu Asp Thr Gly Arg Asn Asp Ser Ser Met His Glu Ala Phe Arg Gly
        35                   40                   45

```
Lys Ile Thr Ala Ile Tyr Ala Leu Gly Arg Thr Asn Asn Ala Asn Asp
 50                  55                  60

Pro Asn Gly His Gly Thr His Val Ala Gly Ser Val Leu Gly Asn Gly
 65                  70                  75                  80

Thr Ser Asn Lys Gly Met Ala Pro Gln Ala Asn Leu Val Phe Gln Ser
                 85                  90                  95

Val Met Asp Ser Asn Gly Gly Leu Gly Gly Leu Pro Ser Asn Val Ser
            100                 105                 110

Thr Leu Phe Ser Gln Ala Tyr Ser Ala Gly Ala Arg Ile His Thr Asn
            115                 120                 125

Ser Trp Gly Ala Pro Val Asn Gly Ala Tyr Thr Thr Asp Ser Arg Asn
130                 135                 140

Val Asp Asp Tyr Val Arg Lys Asn Asp Met Ala Val Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
            195                 200                 205

Gly Pro Thr Lys Asp Gly Arg Ile Lys Pro Asp Val Met Ala Pro Gly
            210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
            275                 280                 285

Leu Ile Ala Gly Ala Thr Asp Ile Gly Leu Gly Tyr Pro Ser Gly Asn
290                 295                 300

Gln Gly Trp Gly Arg Val Thr Leu Asp Lys Ser Leu Asn Val Ala Phe
305                 310                 315                 320

Val Asn Glu Thr Ser Ser Leu Ser Thr Asn Gln Lys Ala Thr Tyr Ser
                325                 330                 335

Phe Thr Ala Gln Ser Gly Lys Pro Leu Lys Ile Ser Leu Val Trp Ser
            340                 345                 350

Asp Ala Pro Ala Ser Thr Ser Ala Ser Val Thr Leu Val Asn Asp Leu
            355                 360                 365

Asp Leu Val Ile Thr Ala Pro Asn Gly Thr Lys Tyr Val Gly Asn Asp
            370                 375                 380

Phe Thr Ala Pro Tyr Asp Asn Asn Trp Asp Gly Arg Asn Asn Val Glu
385                 390                 395                 400

Asn Val Phe Ile Asn Ala Pro Gln Ser Gly Thr Tyr Thr Val Glu Val
                405                 410                 415

Gln Ala Tyr Asn Val Pro Gln Gly Pro Gln Ala Phe Ser Leu Ala Ile
            420                 425                 430

Val Asn

<210> SEQ ID NO 23
<211> LENGTH: 433
<212> TYPE: PRT
```

<213> ORGANISM: Bacillus NCIB12513

<400> SEQUENCE: 23

```
Asn Asp Val Ala Arg Gly Ile Val Lys Ala Asp Val Ala Gln Asn Asn
1               5                   10                  15

Phe Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Ala
65                  70                  75                  80

Thr Asn Lys Gly Met Ala Pro Gln Ala Asn Leu Val Phe Gln Ser Ile
                85                  90                  95

Met Asp Ser Gly Gly Gly Leu Gly Gly Leu Pro Ala Asn Leu Gln Thr
            100                 105                 110

Leu Phe Ser Gln Ala Tyr Ser Ala Gly Ala Arg Ile His Thr Asn Ser
        115                 120                 125

Trp Gly Ala Pro Val Asn Gly Ala Tyr Thr Thr Asp Ser Arg Asn Val
    130                 135                 140

Asp Asp Tyr Val Arg Lys Asn Asp Met Thr Ile Leu Phe Ala Ala Gly
145                 150                 155                 160

Asn Glu Gly Pro Gly Ser Gly Thr Ile Ser Ala Pro Gly Thr Ala Lys
                165                 170                 175

Asn Ala Ile Thr Val Gly Ala Thr Glu Asn Leu Arg Pro Ser Phe Gly
            180                 185                 190

Ser Tyr Ala Asp Asn Ile Asn His Val Ala Gln Phe Ser Ser Arg Gly
        195                 200                 205

Pro Thr Arg Asp Gly Arg Ile Lys Pro Asp Val Met Ala Pro Gly Thr
    210                 215                 220

Tyr Ile Leu Ser Ala Arg Ser Ser Leu Ala Pro Asp Ser Ser Phe Trp
225                 230                 235                 240

Ala Asn His Asp Ser Lys Tyr Ala Tyr Met Gly Gly Thr Ser Met Ala
                245                 250                 255

Thr Pro Ile Val Ala Gly Asn Val Ala Gln Leu Arg Glu His Phe Val
            260                 265                 270

Lys Asn Arg Gly Val Thr Pro Lys Pro Ser Leu Leu Lys Ala Ala Leu
        275                 280                 285

Ile Ala Gly Ala Ala Asp Val Gly Leu Gly Phe Pro Asn Gly Asn Gln
    290                 295                 300

Gly Trp Gly Arg Val Thr Leu Asp Lys Ser Leu Asn Val Ala Phe Val
305                 310                 315                 320

Asn Glu Thr Ser Pro Leu Ser Thr Ser Gln Lys Ala Thr Tyr Ser Phe
                325                 330                 335

Thr Ala Gln Ala Gly Lys Pro Leu Lys Ile Ser Leu Val Trp Ser Asp
            340                 345                 350

Ala Pro Gly Ser Thr Thr Ala Ser Leu Thr Leu Val Asn Asp Leu Asp
        355                 360                 365

Leu Val Ile Thr Ala Pro Asn Gly Thr Lys Tyr Val Gly Asn Asp Phe
    370                 375                 380

Thr Ala Pro Tyr Asp Asn Asn Trp Asp Gly Arg Asn Asn Val Glu Asn
385                 390                 395                 400
```

```
-continued

Val Phe Ile Asn Ala Pro Gln Ser Gly Thr Tyr Thr Val Glu Val Gln
                405                 410                 415

Ala Tyr Asn Val Pro Val Ser Pro Gln Thr Phe Ser Leu Ala Ile Val
            420                 425                 430

His
```